US010718006B2

(12) United States Patent
Dequaire-Rochelet et al.

(10) Patent No.: US 10,718,006 B2
(45) Date of Patent: Jul. 21, 2020

(54) METHODS FOR DETECTING BETA-LACTAMASE-PRODUCING BACTERIA

(71) Applicants: UNIVERSITE DE BOURGOGNE, Dijon (FR); CENTRE HOSPITALIER REGIONAL UNIVERSITAIRE DE DIJON, Dijon (FR); INSTITUT NATIONAL DE LA RECHERCHE AGRONOMIQUE—INRA, Paris (FR)

(72) Inventors: Murielle Dequaire-Rochelet, Dijon (FR); Alain Hartmann, Dijon (FR); Catherine Neuwirth, Dijon (FR); Benoit Chantemesse, Dijon (FR)

(73) Assignees: UNIVERSITE DE BOURGOGNE, Dijon (FR); CENTRE HOSPITALIER REGIONAL UNIVERSITAIRE DE DIJON, Dijon (FR); INSTITUT NATIONAL DE LA RECHERCHE AGRONMIQUE, Paris (FR)

( * ) Notice: Subject to any disclaimer, the term of this patent is extended or adjusted under 35 U.S.C. 154(b) by 33 days.

(21) Appl. No.: 15/562,845

(22) PCT Filed: Apr. 1, 2016

(86) PCT No.: PCT/EP2016/057284
§ 371 (c)(1),
(2) Date: Sep. 28, 2017

(87) PCT Pub. No.: WO2016/156605
PCT Pub. Date: Oct. 6, 2016

(65) Prior Publication Data
US 2018/0105862 A1 Apr. 19, 2018

(30) Foreign Application Priority Data
Apr. 3, 2015 (FR) .................................. 15 52928

(51) Int. Cl.
| | | |
|---|---|---|
| *C12Q 1/34* | (2006.01) | |
| *C12Q 1/04* | (2006.01) | |
| *G01N 27/48* | (2006.01) | |
| *G01N 27/327* | (2006.01) | |

(52) U.S. Cl.
CPC .............. *C12Q 1/34* (2013.01); *C12Q 1/04* (2013.01); *C12Y 305/02006* (2013.01); *G01N 27/3277* (2013.01); *G01N 27/48* (2013.01); *G01N 2333/195* (2013.01); *G01N 2333/986* (2013.01)

(58) Field of Classification Search
None
See application file for complete search history.

(56) References Cited

U.S. PATENT DOCUMENTS

| | | | | |
|---|---|---|---|---|
| 5,641,623 | A * | 6/1997 | Martin | ................ C07D 277/06 424/1.69 |
| 8,097,434 | B2 | 1/2012 | Yang-Woytowitz et al. | |
| 2007/0037153 | A1* | 2/2007 | Mandrand | ................ B82Y 5/00 435/6.12 |
| 2013/0089883 | A1 | 4/2013 | Dallenne et al. | |
| 2014/0308693 | A1 | 10/2014 | Nordmann et al. | |

FOREIGN PATENT DOCUMENTS

WO WO-2015193501 A1 * 12/2015 ....... G01N 33/56911

OTHER PUBLICATIONS

Rochelet et al. Analyst (Apr. 7, 2015) 140: 3551-3556 (Year: 2015).*
Priority document EP 14173161.2 for WO 2015/193501 A1; published Dec. 23, 2015, downloaded from the WIPO website on Feb. 16, 2019. (Year: 2015).*
Laczka et al. Analytica Chimica Acta (2010) 677: 156-161 (Year: 2010).*
International Search Report from International Patent Application No. PCT/EP2016/057284, dated Jun. 24, 2016.
Written Opinion from International Patent Application No. PCT/EP2016/057284, dated Jun. 24, 2016.
Anonymous, "CARBA Test 25: Rapid Detection of Carbapenemase-Producing Enterobacteriaceae Strains", BIO-RAD (2015), accessed Jun. 16, 2016. pp. 1-6. <http://www.bio-rad.com/webroot/web/pdf/inserts/CDG/en/68260_881159_EN.pdf>.
Anonymous, "Beta CARBA Test", BIO-RAD (2015), accessed Jun. 16, 2016. 19 pages. <http://www.bio-rad.com/webroot/web/pdf/WWMSDS/CMD/D/D_D_6826.pdf>.
Chen et al., "Rapid Hydrolysis and Electrochemical Detection of Cephalexin at a Heated Glassy Carbon Electrode" International Journal of Electrochemical Science (2012), vol. 7, pp. 7948-7959.
Hanaki et al., "Characterization of HMRZ-86: A Novel Chromogenic Cephalosporin for the Detection of Extended-Spectrum ⊕-lactamases", Journal of Antimicrobial Chemotherapy (2004), vol. 53, pp. 888-889.
Hanaki et al., "Substrate Specificity of HMRZ-86 for ⊕-lactamases, including Extended-Spectrum ⊕-lactamases (ESBLs)", Japanese Society of Chemotherapy and the Japanese Association for Infectious Diseases (2007), 13(6), pp. 390-395.
Hrabák et al., "Carbapenemase Activity Detection by Matrix-Assisted Laser Desorption Ionization—Time of Flight Mass Spectrometry", Journal of Clinical Microbiology (2011), 49(9), pp. 3222-3227.
Mittelmann et al., "Amperometric Quantification of Total Coliforms and Specific Detection of *Escherichia coli*", Analytical Chemistry (2002), 74(4), pp. 903-907.
Moreira Gonçalves et al., "Penicillinase-Based Amperometric Biosensor for Penicillin G", Electrochemistry Communications (2014), vol. 38, pp. 131-133.
Nordmann et al., "Rapid Detection of Extended-Spectrum-⊕-Lactamases-Producing Enterobacteriaceae", Journal of Clinical Microbiology (2012), 50(9), pp. 3016-3022.

(Continued)

*Primary Examiner* — Susan M Hanley
(74) *Attorney, Agent, or Firm* — Greer, Burns & Crain, Ltd.

(57) ABSTRACT

An electrochemical method is provided for in-vitro determination of the presence of bacteria producing lactamases, in a sample that may contain such bacteria.

13 Claims, 8 Drawing Sheets

(56) References Cited

OTHER PUBLICATIONS

O'Callaghan et al., "Novel Method for Detection of ⊕-Lactamases by Using A Chromogenic Cephalosporin Substrate", Antimicrobial Agents and Chemotherapy (1972), 1(4), pp. 283-288.

Pires et al., "Blue-Carba, an Easy Biochemical Test for Detection of Diverse Carbapenemase Producers Directly from Bacterial Cultures", Journal of Clinical Microbiology (2013), 51(12), pp. 4281-4283.

Sparbier et al., "Matrix-Assisted Laser Desorption Ionization—Time of Flight Mass Spectrometry-Based Functional Assay for Rapid Detection of Resistance Against ⊕-Lactam Antibiotics", Journal of Clinical Microbiology (2012), 50(3), pp. 927-937.

* cited by examiner

___ K12
___ Inducible cephalosporinase
...... Penicillinase
---- Carbapenemase
----- ESBL
---- Hyperproduced cephalosporinase

METHODS FOR DETECTING BETA-LACTAMASE-PRODUCING BACTERIA

BACKGROUND

The present invention relates to a method for detecting, in a sample or a culture medium, the presence of bacteria that are resistant to the beta-lactam antibiotics through their ability to produce beta-lactamases.

The beta-lactam antibiotics, which comprise the penicillins, monobactams, cephalosporins and carbapenems, are antibiotics that act by inhibiting the synthesis of the peptidoglycan. These are molecules often used in first-line treatment of serious infections both in general practice and in hospital medicine. The beta-lactamases are enzymes that hydrolyse the beta-lactam ring of the beta-lactam antibiotics. This is the most common mechanism of resistance to beta-lactam antibiotics. According to Ambler (Ambler, R. P. *Philos. Trans. R. Soc. London Ser B*, 1980, 289, 321-331), the beta-lactamases are classified in 4 groups:

A: penicillinases, including extended broad-spectrum beta-lactamases (ESBLs)
B: metallo-enzymes
C: cephalosporinases
D: oxacillinases In the enterobacteria, the production of extended-spectrum beta-lactamases (designated ESBLs hereinafter) or of hyperproduced cephalosporinases is currently the principal mechanism of resistance to third-generation cephalosporins (designated C3G hereinafter), such as cefotaxime, ceftriaxone or ceftazidime, which are the oxyimino-cephalosporins. Cefepime, which is the only fourth-generation cephalosporin (designated C4G hereinafter), is hydrolyzed by the ESBLs but not usually by the cephalosporinases. The penicillins are also hydrolyzed, but not the carbapenems. The activity of the ESBLs may be inhibited by clavulanic acid, tazobactam or sulbactam (penicillinase inhibitors). The activity of the cephalosporinases may be inhibited by cloxacillin. The carbapenemases (enzymes that may belong to families A, B and D according to Ambler) are enzymes that hydrolyse the carbapenems but usually also the penicillins and the cephalosporins.

The fast, accurate detection of bacteria that are resistant to the third-generation cephalosporins, producers of ESBLs or of hyperproduced cephalosporinases, or of carbapenemases, is crucial for patient management. It should lead to the establishment of suitable antibiotic treatment. In the absence of production of enzymes that hydrolyse the C3Gs, the latter can be used in first-line treatment, whereas otherwise it becomes necessary to resort to the carbapenems. In this case it is also necessary to determine whether these bacteria produce carbapenemases.

At present, the conventional technique used for detecting beta-lactamase-producing bacteria is based on the implementation of an antibiogram and the application of the double disc synergy test, which makes it possible to demonstrate the restoration of sensitivity to C3Gs in the presence of a penicillinase inhibitor. Despite its efficacy, implementation of this technique requires a preliminary step of culturing and isolating the bacteria, which means a delay of at least 24 hours before the production of beta-lactamases is detectable.

The presence of beta-lactamase-producing bacteria may also be demonstrated by methods of molecular biology, for example using PCR and/or sequencing to detect the genes coding for the beta-lactamases. Although they may allow specific characterization of the genes coding for example for the ESBLs, these laboratory techniques are expensive and take quite a long time because of the preliminary extraction of DNA from complex samples.

There is therefore an urgent need in the field of health care to develop a method that is effective, quick and inexpensive for detecting the presence of beta-lactamase-producing bacteria, in order to detect the presence of the bacterial strains that are resistant to beta-lactam antibiotics.

Nordmann et al. (*J. Clin. Microbiol.*, 2012, 50, 3016-3022) describe a method for detecting ESBL-producing bacteria that involves the use of cefotaxime and a pH colour indicator. This method is based on the fact that hydrolysis of the beta-lactam ring of cefotaxime leads to the formation of a carboxylic acid function and therefore to acidification of the reaction medium. The change in pH of the medium is visualized through the use of a colour indicator.

Despite its efficacy and speed, this method first requires a limiting step of isolating the bacterial strains.

Another colorimetric approach consists of using nitrocefin, a chromogenic cephalosporin, which can be hydrolyzed by all the beta-lactamases, thus causing a colour change from yellow to red (O'Callaghan et al., *Antimicrob. Agents Chemother.*, 1972, 1, 283-288). FIG. 11 illustrates hydrolysis of the beta-lactam ring of nitrocefin by a beta-lactamase. More recently, another chromogenic cephalosporin called HMRZ-86 (Hanaki et al., *Antimicrob. Agents Chemother.*, 2004, 53, 888-889) has been proposed for detecting bacterial strains resistant to C3Gs, based on the same principle.

However, this method once again requires the use of previously isolated bacterial strains to allow colorimetric detection. This method cannot be used directly on complex samples having a coloration that may interfere with colorimetric detection of the hydrolysis of nitrocefin. Once again, this method involves a delay of at least 24 hours between taking a clinical sample and delivering the result.

In recent years, the MALDI-TOF mass spectrometry technique has also been proposed for detecting the products of hydrolysis of the beta-lactam antibiotics after incubation of the latter in the presence of beta-lactamase-producing strains (Hrabák et al. *J. Clin. Microbiol.* 2011, 49, 3222-3227; Sparbier et al., *J. Clin. Microbiol.*, 2012, 50, 927-937). However, this laboratory technique, which must also be implemented with previously isolated strains, is still expensive and requires qualified personnel for interpreting the mass spectra.

Moreover, Gonçalves et al. (*Electrochemistry Communication* 38 (2014) 131-133) have an amperometric biosensor for detecting penicillin G by amperometric measurement of the pH change of the medium linked to hydrolysis of penicillin G to penicilloic acid by penicillinase. Since penicillin G and penicilloic acid are not electrically active, amperometric measurement is carried out in the presence of cobalt, which plays the role of redox mediator.

Chen et al. (*Int. J. Electrochem. Sci.*, 7 (2012) 7948-7959) describe a method for detecting cephalexin electrochemically, after its hydrolysis, achieved after an oxygen-free alkaline solution of cephalexin is heated in the dark at 70° C. The products of hydrolysis of cephalexin (cleavage of the C—C=O bond of the β-lactam ring) described in that document were produced under quite specific extreme conditions and cannot be obtained by incubating cephalexin with a beta-lactamase, which in its case cleaves the β-lactam ring at the level of the amide bond.

To date, the prior art does not describe any substrate of the beta-lactamases or any product resulting from hydrolysis by a beta-lactamase having electrically active properties.

SUMMARY

Now, the inventors have discovered that certain substrates of the beta-lactamases and/or the product of their hydrolysis by a beta-lactamase have electrically active properties.

In this context, the objective of the invention is therefore to provide an electrochemical method capable of rapid and efficient determination of the presence of beta-lactamase-producing bacteria in a sample without isolating the bacterial strains beforehand.

The invention relates to a method for in-vitro determination of the presence of beta-lactamase-producing bacteria in a sample that may contain said bacteria, comprising the following steps:

(a) incubating said sample in a medium containing a substrate of the beta-lactamases having electrochemical properties, in particular a beta-lactam antibiotic having electrochemical properties, more particularly a cephalosporin, as substrate of the beta-lactamases, (b) applying a means of electrochemical analysis in order to determine the presence of the beta-lactamase-producing bacteria.

The invention is based on the fact that certain substrates of the beta-lactamases can be detected electrochemically after they have been hydrolyzed by a beta-lactamase.

In particular, hydrolysis of the beta-lactam ring of a beta-lactam antibiotic by a beta-lactamase can be detected electrochemically.

In the context of the present invention, a beta-lactam antibiotic having electrochemical properties is in particular a cephalosporin, more particularly nitrocefin or the compound HMRZ-86 (E isomer of (6R,7R)-trifluoroacetate 7-[[2-(2-amino-4-thiazolyl)-2-[(1-carboxy-1-methylethoxy)imino]acetyl]amino]-1-aza-3-[2-(2,4-dinitrophenyl)ethenyl]-8-oxo-5-thiabicyclo[4.2.0]oct-2-ene-2-carboxylic acid).

In the context of the present invention, such a substrate of the beta-lactamases having electrochemical properties may also be the substrate (reagent R2) of the β CARBA™ kit marketed by Bio-rad.

Nitrocefin can be hydrolyzed by all types of β-lactamases, whereas the compound HMRZ-86 is only degraded by the bacteria that are resistant to the C3Gs; i.e. producing ESBLs, hyperproduced cephalosporins and carbapenemases. The substrate (reagent R2) of the β CARBA™ kit is only hydrolyzed by the carbapenemase-producing bacteria.

The inventors have demonstrated for the first time that the electrochemical properties of certain substrates of the beta-lactamases, in particular certain beta-lactam antibiotics, such as nitrocefin or the compound HMRZ-86, are quite distinct from those of these hydrolyzed substrates. For example, hydrolyzed nitrocefin is an electrically active product capable of generating a specific anodic oxidation current that is measurable by an electrochemical method. The oxidation of hydrolyzed nitrocefin generates an anodic current in a potential range different from that in which said anodic current corresponding to the oxidation of nitrocefin appears. Thus, the anodic current specific to hydrolyzed nitrocefin can be used as the analytical response indicating the presence of nitrocefin hydrolyzed by a beta-lactamase.

In contrast to the methods already developed in the prior art, which require culturing the bacteria for at least 24 hours beforehand, the method described in the invention makes it possible to detect the presence or absence of beta-lactamase-producing bacteria after just a few hours of incubation of the sample, in particular from 1 to 4 hours, before implementing the electrochemical measurement.

As an example, the incubation time of a sample with a medium containing nitrocefin is typically from 5 to 30 minutes.

A medium containing a substrate of the beta-lactamases having electrochemical properties may be a buffered medium, to which an electrically active substrate of the beta-lactamases is added. Said buffered medium may be, as an example, a phosphate buffer of pH 7, at a concentration of 100 mM.

By "beta-lactamases" is meant a family of enzymes capable of hydrolyzing the β-lactam ring of a β-lactam antibiotic. The penicillins, cephalosporins, monobactams and carbapenems are the four families of β-lactam antibiotics.

Based on their catalytic properties and their affinity for certain substrates as well as their sensitivity to certain types of beta-lactamase inhibitors, the main beta-lactamases are as follows: penicillinases, inducible cephalosporinases, hyperproduced cephalosporinases, extended-spectrum beta-lactamases, and carbapenemases.

By "penicillinases" is meant the enzymes that hydrolyse the amino-, carboxy- and ureidopenicillins. They are inhibited by penicillinase inhibitors, which are clavulanic acid, tazobactam and sulbactam.

By "inducible cephalosporinases" is meant the enzymes that hydrolyse the amino-penicillins and the 1st and/or 2nd generation cephalosporins. They are not sensitive to the action of the penicillinase inhibitors; on the other hand, they are inhibited by cloxacillin. Expression of a gene coding for a cephalosporinase may be induced by an inducer, which may in particular be a beta-lactam antibiotic.

By "hyperproduced cephalosporinases" is meant the enzymes that hydrolyse the aminopenicillins, the carboxy- and ureidopenicillins, the cephalosporins of 1st, 2nd, 3rd or even of 4th generation. They are not sensitive to the action of the penicillinase inhibitors; however, they are inhibited by cloxacillin. Expression of these enzymes is derepressed and leads to production of these enzymes in abundance.

By "extended-spectrum beta-lactamases (ESBLs)" is meant the enzymes that hydrolyse the amino-, carboxy- and ureidopenicillins, the cephalosporins of 1st, 2nd, 3rd and 4th generation, and are sensitive to inhibition of the penicillinase inhibitors.

By "carbapenemases" is meant the enzymes that have a hydrolytic activity on the carbapenems but generally also on the penicillins and the cephalosporins of 1st, 2nd, 3rd and 4th generation.

According to the invention, the beta-lactamases can be produced in particular by Gram-negative bacteria:

i) of the Enterobacteriaceae family, in particular of the genera *Escherichia* (in particular *Escherichia coli*), *Klebsiella, Enterobacter, Serratia, Morganella, Proteus, Providencia, Pantoea, Hafnia, Citrobacter, Salmonella, Shigella* and *Yersinia*.

ii) non-fermenting, in particular *Pseudomonas* (in particular *P. aeruginosa*), *Stenotrophomonas* and *Achromobacter*.

iii) *Acinetobacter* (in particular *A. baumannii*).

In a particular embodiment, the aforesaid method of the invention further comprises, before implementing step (a), a step for concentrating the bacteria present in a sample that may contain them. The bacteria may be concentrated, for example, by filtration or centrifugation.

In a particular embodiment, step (a) of the aforesaid method of the invention is implemented in a medium containing a substrate of the beta-lactamases having electrochemical properties, in particular a beta-lactam antibiotic having electrochemical properties, in particular nitrocefin, the compound HMRZ-86 or the substrate (reagent R2) of the β CARBA™ kit. A person skilled in the art will know how to select a suitable concentration for said substrate.

According to the invention, a means of electrochemical analysis for implementing the invention may be potentiometric measurement, impedance measurement, coulometric measurement or amperometric measurement.

In an advantageous embodiment, the electrochemical analysis is implemented by amperometric measurement.

By "amperometric measurement" is meant measurement of the electric current as a function of a potential difference established between the working electrode and the reference electrode.

The electric current may be measured by the known amperometric techniques, preferably by potential scanning voltammetry, which may be linear, cyclic, pulsed, or of the potential step type, such as chronoamperometry.

In a particularly advantageous embodiment of the invention, the presence of a hydrolyzed beta-lactamase substrate is measured by cyclic or linear voltammetry.

Implementation of these techniques requires a set-up that may have two or even three electrodes, i.e. a set-up comprising a working electrode, a reference electrode and optionally an auxiliary electrode (counter-electrode). The working electrode, the surface of which serves as the site for electron transfer, may be based on carbon or based on a noble metal or based on metal oxide. The reference electrode is an electrode the potential of which is constant, which makes it possible to apply a precisely defined potential to the working electrode. The reference electrode may be an Ag/AgCl electrode. The counter-electrode, which makes it possible to establish the passage of the electric current with the working electrode, may be made with an inert material, such as platinum or carbon. A person skilled in the art will know how to select and combine the appropriate electrodes based on his general knowledge.

Concerning the method of manufacture of the electrodes, the screen printing technique is preferable, although other methods of industrial manufacture such as rotogravure, inkjet printing or optionally photolithography may be envisaged. The electrodes obtained by screen printing are particularly suitable as they can be mass produced at low cost, and may therefore optionally be single-use. Moreover, their geometric shape as well as their size can be varied easily. These electrodes may be screen-printed in the form of a sensor and optionally incorporated at the bottom of the wells of a microplate or other supports or systems allowing filtration of the bacterial suspensions and incubation with nitrocefin or another substrate of the beta-lactamases having electrochemical properties.

In a particular embodiment, the amperometric measurement is implemented with a screen-printed sensor. This makes it possible to carry out the measurement in a small volume of solution of the order of a few microlitres.

In a particular embodiment, the amperometric measurement is implemented with a device involving three electrodes: an Ag/AgCl reference electrode, a working electrode made of carbon and a counter-electrode made of carbon.

In another particular embodiment, the amperometric measurement is implemented with a screen-printed sensor comprising an Ag/AgCl reference electrode, a working electrode made of carbon and a counter-electrode made of carbon.

The presence of a hydrolyzed substrate, for example hydrolyzed nitrocefin, is indicated by the presence of an anodic oxidation current in a potential range and the absence of said current for a control that lacks said hydrolyzed substrate.

When a hydrolyzed substrate, in particular a hydrolyzed beta-lactam antibiotic, for example hydrolyzed nitrocefin, undergoes measurement by cyclic voltammetry, its presence is indicated by a peak of anodic oxidation current specific to the hydrolyzed substrate in a defined potential range.

For example, when detection is carried out by cyclic voltammetry using an Ag/AgCl reference electrode in a buffer of neutral pH containing, for example, nitrocefin, the intensity related to the peak current of anodic oxidation corresponding to the oxidation of hydrolyzed nitrocefin is measured in a potential range comprised between +0.1 V and +0.5 V, in particular between +0.2 V and +0.4 V, more particularly between +0.23 V and +0.33 V.

In particular, when detection is carried out by cyclic voltammetry in a phosphate buffer of pH 7 containing nitrocefin, the peak current of anodic oxidation related to the oxidation of hydrolyzed nitrocefin is located at +0.3 V vs. Ag/AgCl.

When another type of reference electrode and/or another reaction medium is used for implementing the method of the invention, a person skilled in the art will know how to calculate or identify this potential range based on his general knowledge.

Since the presence of a hydrolyzed substrate, for example hydrolyzed nitrocefin or the hydrolyzed compound HMRZ-86, is detected by an electrochemical method, the method described in the invention proves particularly advantageous for analyzing coloured or turbid samples without preliminary treatment, with the possibility of offering quantified measurement with good sensitivity by means of inexpensive equipment, having a reduced size, and optionally portable.

A sample that can be analyzed by the method of the invention may be a biological sample, a sample of environmental origin or a food sample.

A biological sample may be in particular a blood sample, a urine sample, a tissue sample or a lung sample.

A sample of environmental origin may be wastewater, hospital wastewater, treated wastewater or sludges originating from wastewater treatment, as well as residues from wet or dry methanation reactors (digestates).

A food sample may be products and by-products of animal origin and more particularly of avian origin such as poultry, which may contain beta-lactamase-resistant bacteria.

In particular, the method of the invention comprises the following steps:

(a) incubating a sample that may contain said bacteria in a medium containing a substrate of the beta-lactamases, in particular a beta-lactam antibiotic, having electrochemical properties, (b) applying an amperometric measurement to the aforesaid medium obtained at the end of step (a) and to a negative control, respectively, (c) determining the presence of the beta-lactamase-producing bacteria by comparing the value of the intensity of the anodic current corresponding to oxidation of the hydrolyzed substrate, in particular of the hydrolyzed beta-lactam antibiotic, measured for the aforesaid medium obtained at the end of step (a), with the value of the intensity of the anodic current measured for the negative control.

According to the invention, a negative control is a medium containing said substrate in the absence of a sample.

More particularly, the method of the invention comprises the following steps:

(a) incubating a sample that may contain said bacteria in a medium containing nitrocefin, (b) applying an amperometric measurement to the aforesaid medium obtained at the end of step (a) and to a negative control, respectively, (c) determining the presence of the beta-lactamase-producing bacteria by comparing the value of the intensity of the anodic current corresponding to the oxidation of hydrolyzed nitrocefin measured for the aforesaid medium obtained at the end of step (a), with the value of the intensity of the anodic current measured for the negative control.

An amperometric measurement applied to said negative control makes it possible to indicate any current that is not associated with the oxidation of hydrolyzed nitrocefin.

During amperometric measurement, the presence of hydrolyzed nitrocefin is indicated by the appearance or increase of an anodic current in a defined potential range relative to the anodic current of the control measured in the same range.

Moreover, the method described in the present invention offers the possibility of quantifying the beta-lactamase-producing bacteria in a sample.

In fact, the intensity of the anodic current produced by the oxidation of a hydrolyzed substrate, in particular of hydrolyzed nitrocefin, is quantitatively proportional to the quantity of hydrolyzed nitrocefin. When the quantity of the substrate is in excess, the quantity of the hydrolyzed substrate is also proportional to the quantity of beta-lactamases involved in the hydrolysis of said substrate, as well as to the quantity of the bacteria producing these enzymes. Consequently, by comparing the value of the intensity of the anodic current specific to the hydrolyzed substrate with a reference value, read on a calibration curve, it is possible to determine the quantity of beta-lactamase-producing bacteria.

A particular embodiment of the invention makes it possible both to determine the presence of beta-lactamase-producing bacteria in a sample that may contain them, and to quantify them.

In this embodiment, the method further comprises, after determination of the presence of beta-lactamase-producing bacteria, a step consisting of comparing the value of the intensity of the anodic current measured for the aforesaid medium obtained at the end of step (a) with a calibration curve established under the same conditions.

Said calibration curve is established by serial dilution of a reference sample containing a known quantity of beta-lactamase-producing bacteria and determined beforehand by any conventional method, such as for example counting on a culture medium or real-time PCR.

In a particular embodiment, the invention relates to a method allowing determination and quantification of the beta-lactamase-producing bacteria in a sample that may contain said bacteria, said method comprising:

(a) incubating a sample that may contain said bacteria in a medium containing a substrate of the beta-lactamases, in particular a beta-lactam antibiotic, having electrochemical properties, (b) applying an amperometric measurement to the aforesaid medium obtained at the end of step (a) and to a negative control, respectively, (c) determining the presence of the beta-lactamase-producing bacteria by comparing the value of the intensity of the anodic current corresponding to oxidation of the hydrolyzed substrate, in particular of the hydrolyzed beta-lactam antibiotic, measured for the aforesaid medium obtained at the end of step (a), with the value of the intensity of the anodic current measured for the negative control;

(d) comparing the value of the intensity of the anodic current measured for the aforesaid medium obtained at the end of step (a) with a calibration curve established under the same conditions for quantifying said bacteria.

Depending on the specificity of the substrates having electrochemical properties, the method of the invention may be implemented for specifically determining in vitro the presence of bacteria producing one or more types of beta-lactamases.

In a particular embodiment, the method of the invention makes it possible to determine and quantify in vitro the presence of bacteria resistant to a third-generation cephalosporin, said method implementing, in step (a), a beta-lactam antibiotic that is only hydrolyzed by the extended-spectrum beta-lactamases, the hyperproduced cephalosporinases and the carbapenemases, in particular the compound HMRZ-86 (E isomer of (6R,7R)-trifluoroacetate 7-[[2-(2-amino-4-thiazolyl)-2-[(1-carboxy-1-methylethoxy)imino]acetyl]amino]-1-aza-3-[2-(2,4-dinitrophenyl)ethenyl]-8-oxo-5-thiabicyclo[4.2.0]oct-2-ene-2-carboxylic acid).

In another particular embodiment, the method of the invention makes it possible to determine and quantify in vitro the presence of carbapenemase-producing bacteria, said method using, in step (a), a substrate that is only hydrolyzed by the carbapenemases, in particular the substrate (reagent R2) of the β CARBA™ kit marketed by Bio-rad.

In another particular embodiment, using nitrocefin and at least one other beta-lactam antibiotic and at least one inhibitor of a beta-lactamase, the method of the invention also makes it possible to distinguish the type of beta-lactamases produced by the aforesaid bacteria in a sample that may contain them.

In fact, the inventors found that, in a series of culture media containing, respectively, a substrate that is specific to and optionally an inhibitor that is specific to a type of beta-lactamase, the bacteria producing the different types of beta-lactamases may give, respectively, a profile that is specific in terms of intensities of the anodic current for hydrolyzed nitrocefin when implementing an amperometric measurement.

One of the advantages of this embodiment is that it makes it possible to distinguish the beta-lactamases in complex, coloured matrices without isolating the bacteria beforehand.

More particularly, a method of the invention additionally makes it possible to distinguish the type of beta-lactamases selected from penicillinases, extended-spectrum beta-lactamases, inducible cephalosporinases, hyperproduced cephalosporinases and carbapenemases, produced by the aforesaid bacteria in a sample that may contain them, said method comprising the following steps:

(a) incubating, in parallel, a fraction of the aforesaid sample in a culture medium A, a culture medium B and a culture medium C:

culture medium A being a basic culture medium, culture medium B being a basic culture medium supplemented with a third-generation cephalosporin, and culture medium C being a basic culture medium supplemented with a cephalosporin and a penicillinase inhibitor, and optionally in a culture medium B', a culture medium C', a culture medium D, a culture medium E:

culture medium B' being a basic culture medium supplemented with a third-generation cephalosporin different from that present in medium B;

culture medium C' being culture medium B' supplemented with a penicillinase inhibitor;

culture medium D being a basic culture medium supplemented with a cephalosporin and a cephalosporinase inhibitor, and culture medium E being a basic culture medium supplemented with a carbapenem, (b) incubating, in parallel, the aforesaid culture media obtained at the end of the incubation in step (a) in a medium containing nitrocefin;

(c) applying an amperometric means to the aforesaid media obtained at the end of step (b) in order to determine the presence of beta-lactamase-producing bacteria and to distinguish the type of beta-lactamases.

According to the invention, a basic culture medium may be any type of culture medium used conventionally for incubating bacteria, such as LB medium (Luria Bertani broth), TSB (Tryptone Soy Broth) or BHI (Brain Heart Infusion).

In a particular embodiment, before the implementation of step (b) and after step (a), the aforesaid method of the invention further comprises a step for concentrating the bacteria present in the culture media in order to give a more significant catalytic response. The bacteria may be concentrated, for example, by filtration or by centrifugation.

According to the invention, said third-generation cephalosporin is selected from cefotaxime, ceftazidime and ceftriaxone; said carbapenem is selected from ertapenem, imipenem or meropenem.

According to the invention, said penicillinase inhibitor is in particular selected from clavulanic acid, tazobactam or sulbactam; said cephalosporinase inhibitor is in particular cloxacillin.

Culture medium B or B' makes it possible to inhibit the growth of the bacteria producing penicillinases or inducible cephalosporinases.

Culture medium C or C' makes it possible to inhibit the growth of the bacteria producing a penicillinase or an extended-spectrum beta-lactamase. In a particular embodiment, a culture medium C is a culture medium B supplemented with a penicillinase inhibitor.

Culture medium D makes it possible to inhibit the growth of the bacteria producing an inducible or hyperproduced cephalosporinase.

Culture medium E makes it possible to inhibit the growth of the bacteria producing any beta-lactamase except a carbapenemase.

Use of the media B, B', C and C' makes it possible to distinguish the ESBL-producing bacteria that are sensitive to a third-generation cephalosporin, for example cefotaxime, but resistant to another third-generation cephalosporin, for example ceftazidime, or vice versa.

After respective incubation of the fractions of one and the same sample in culture media A, B, C, and optionally media B', C', D and E, the beta-lactamases produced by the bacteria originating from these fractions are different. The present invention makes it possible to show this difference by an amperometric method that indicates the quantity of nitrocefin hydrolyzed by these beta-lactamases by the values of the intensity of the anodic current corresponding to the oxidation of hydrolyzed nitrocefin.

The values $i_A$, $i_B$, $i_B'$, $i_C$, $i_C'$, $i_D$, and $i_E$ are the values of the intensity of the anodic current corresponding to the oxidation of the hydrolyzed nitrocefin measured for the bacteria from culture media A, B, B', C, C', D and E, respectively.

In the context of the method of the invention, a penicillinase is characterized by the presence of the currents specific to hydrolyzed nitrocefin obtained for the bacteria originating from a medium A, from a medium B and optionally from a medium B', and the absence of the specific current for the bacteria originating from a medium C and optionally from a medium C'. The value is may be either below or above the value $i_B$ and optionally $i_B'$.

An ESBL is characterized by a high intensity of the anodic current specific to hydrolyzed nitrocefin obtained for the bacteria originating from a medium A, from a medium B and optionally from a medium B', respectively, and the absence of this specific current for the bacteria from a medium C and optionally from a medium C'. The values $i_B$ and optionally are close to the value An inducible cephalosporinase is characterized by an anodic current specific to hydrolyzed nitrocefin obtained for the bacteria originating from media A, B and optionally B', C and optionally C', with $i_A < i_B < i_C$ and optionally $i_A < i_B' < i_C'$, and the absence of this specific current for the bacteria originating from a medium D.

A hyperproduced cephalosporinase is characterized by a high intensity of the anodic current specific to hydrolyzed nitrocefin obtained for the bacteria originating from a medium A, the presence of this specific current for the bacteria originating from a medium B and from a medium C, optionally from a medium B' and from a medium C', respectively, with $i_B > i_C$ and optionally $i_B' > i_C'$, and the absence of this specific current for the bacteria from a medium D.

A carbapenemase is characterized by the presence of an anodic current specific to hydrolyzed nitrocefin obtained for the bacteria from media A, B and optionally B', C and optionally C', D and E.

In a more particular embodiment, the invention relates to a method in order to determine the presence of the bacteria producing an extended-spectrum beta-lactamase, said method comprising the following steps:

(a) incubating, in parallel, a fraction of the aforesaid sample in a culture medium A, a culture medium B and a culture medium C as previously defined, (b) incubating, in parallel, the aforesaid culture media obtained at the end of the incubation in step (a) in a medium containing nitrocefin, (c) applying an amperometric means to the aforesaid media obtained at the end of step (b) in order to determine the presence of the bacteria producing an extended-spectrum beta-lactamase.

In another more particular embodiment, the invention relates to a method for determining the presence of the bacteria producing an extended-spectrum beta-lactamase, said method comprising the following steps:

(a) incubating, in parallel, a fraction of the aforesaid sample in a culture medium A, a culture medium B, a culture medium B', a culture medium C and a culture medium C', as previously defined, (b) incubating, in parallel, the aforesaid culture media obtained at the end of the incubation in step (a) in a medium containing nitrocefin, (c) applying an amperometric means to the aforesaid media obtained at the end of step (b) in order to determine the presence of the bacteria producing an extended-spectrum beta-lactamase.

Use of the media B, B', C and C' makes it possible to distinguish the ESBL-producing bacteria that are sensitive to a third-generation cephalosporin but resistant to another third-generation cephalosporin.

In a particular embodiment, culture medium B is culture medium A supplemented with cefotaxime; culture medium B' is culture medium A supplemented with ceftazidime; culture medium C is culture medium B supplemented with a penicillinase inhibitor; culture medium C' is culture medium B' supplemented with a penicillinase inhibitor.

In another particular embodiment, culture medium B is culture medium A supplemented with ceftazidime; culture medium B' is culture medium A supplemented with cefotaxime; culture medium C is culture medium B supplemented with a penicillinase inhibitor; culture medium C' is culture medium B' supplemented with a penicillinase inhibitor.

Use of these media in the context of the invention makes it possible to distinguish the ESBL-producing bacteria that are either sensitive to cefotaxime but resistant to ceftazidime or are resistant to cefotaxime but sensitive to ceftazidime.

Advantageously, said method in order to determine the presence of beta-lactamase-producing bacteria and to distinguish the type of beta-lactamases comprises the following steps:

(a) incubating, in parallel, a fraction of the aforesaid sample in a culture medium A, a culture medium B, a culture medium B', a culture medium C and a culture medium C':
  culture medium A being a basic culture medium,
  culture medium B and culture medium B' being basic culture media supplemented, respectively, with a different third-generation cephalosporin,
  culture medium C and culture medium C' being, respectively, culture media B and B' supplemented with a penicillinase inhibitor,
and optionally in a culture medium D, a culture medium E:
  culture medium D being a basic culture medium supplemented with a cephalosporin and a cephalosporinase inhibitor, and
  culture medium E being a basic culture medium supplemented with a carbapenem, (b) incubating, in parallel, the aforesaid culture media obtained at the end of the incubation in step (a) in a medium containing nitrocefin;

(c) applying an amperometric means to the aforesaid media obtained at the end of step (b) in order to determine the presence of beta-lactamase-producing bacteria and to distinguish the type of beta-lactamases.

According to another more particular embodiment, the method of the invention makes it possible to determine and distinguish the beta-lactamase-producing bacteria in a sample that may contain them, said method comprising the following steps:

(a) incubating, in parallel, a fraction of the aforesaid sample in a culture medium A, a culture medium B, a culture medium C, a culture medium D, a culture medium E, optionally a medium B' and a medium C', as previously defined, (b) incubating, in parallel, the aforesaid culture media obtained at the end of the incubation in step (a) in a medium containing nitrocefin, (c) applying an amperometric measurement to the aforesaid media obtained at the end of step (b) and to a negative control, respectively, (d) determining the presence of beta-lactamase-producing bacteria in the aforesaid sample by comparing the value of the intensity of the anodic current corresponding to the oxidation of hydrolyzed nitrocefin obtained for the fraction cultured in culture medium A with the value of the intensity of the current obtained for the negative control, and (e) distinguishing the type of beta-lactamases produced by the aforesaid bacteria in said sample, by comparing the respective values of the intensity of the aforesaid anodic current obtained for the fractions cultured in parallel in culture media A, B, C, D and E, optionally B' and C' with the respective values obtained for a reference bacterial strain.

By "reference bacterial strain" is meant a bacterial strain producing a beta-lactamase the type of which has already been identified.

In an even more particular embodiment, the method of the invention further comprises a step (f) after step (e) making it possible to quantify bacteria producing the beta-lactamase distinguished in step (e) by comparing the value of the intensity of the anodic current corresponding to nitrocefin hydrolyzed by said beta-lactamase with a calibration curve established under the same conditions.

The value of the intensity of the anodic current corresponding to nitrocefin hydrolyzed by an extended-spectrum beta-lactamase is calculated according to the formula: $i_B - i_C$.

The value of the intensity of the anodic current corresponding to nitrocefin hydrolyzed by a hyperproduced cephalosporinase is calculated according to the formula: $i_B - i_D$.

The value of the intensity of the anodic current corresponding to nitrocefin hydrolyzed by a carbapenemase corresponds to the value $i_E$.

More advantageously, the method of the invention can even distinguish the bacteria producing a beta-lactamase subfamily, using an additional medium containing a substrate and an inhibitor specific to a subfamily of a beta-lactamase.

The method of the invention can in particular distinguish the bacteria producing a carbapenemase subfamily, using an additional medium containing a carbapenem and an inhibitor specific to a subfamily of carbapenemases.

Distinguishing is based on the specific sensitivity of a carbapenemase subfamily to certain types of inhibitors. For example, the metallo-beta-lactamases, a subfamily of carbapenemases belonging to family B according to Ambler, are sensitive to EDTA or to mercaptoacetic acid, whereas the carbapenemases of family A according to the Ambler classification are sensitive to clavulanic acid and to boronic acid.

According to the invention, a carbapenemase inhibitor is selected from EDTA, mercaptoacetic acid, boronic acid, or clavulanic acid.

In another advantageous embodiment, the method of the invention makes it possible to distinguish the type of beta-lactamases and optionally to specify the subfamily of carbapenemases produced by the aforesaid bacteria in a sample that may contain them, said method comprising the following steps:

(a) incubating, in parallel, a fraction of the aforesaid sample:
  in a culture medium A, a culture medium B and a culture medium C, as previously defined, and
  optionally in a culture medium B', a culture medium C', a culture medium D, a culture medium E, and a culture medium F, culture media B', C', D, E being as previously defined, culture medium F being a basic culture medium supplemented with a carbapenem and an inhibitor specific to a subfamily of carbapenemases;

(b) incubating, in parallel, the aforesaid culture media obtained at the end of step (a) in a medium containing nitrocefin, (c) applying a means of electrochemical analysis to the aforesaid media obtained at the end of step (b) in order to determine the presence of beta-lactamase-producing bacteria and to distinguish the type of beta-lactamases.

Culture medium F makes it possible to inhibit the growth of bacteria producing a type of carbapenemase that is sensitive to the aforesaid inhibitor specific to a subfamily of carbapenemases: EDTA and mercaptoacetic acid are specific inhibitors of family B whereas boronic acid and clavulanic acid are specific inhibitors of family A.

In a particularly advantageous embodiment, the method of the invention for distinguishing the type of beta-lactamases and optionally defining the subfamily of carbapenemases produced by the aforesaid bacteria comprises the following steps:

(a) incubating, in parallel, a fraction of the aforesaid sample in a culture medium A, a culture medium B, a culture medium C, a culture medium D, a culture medium E, and a culture medium F, as previously defined, and optionally a culture medium B' and a culture medium C' as previously defined, (b) incubating, in parallel, the aforesaid culture media obtained at the end of the incubation in step (a) in a medium containing nitrocefin, (c) applying an amperometric measurement to the aforesaid media obtained at the end of step (b) and to a negative control, respectively, (d) determining the presence of beta-lactamase-producing bacteria in said sample by comparing the value of the intensity of the anodic current corresponding to the oxidation of hydrolyzed nitrocefin obtained for the fraction cultured in culture medium A with the value of the intensity of the current obtained for the negative control, (e) distinguishing the type of beta-lactamases produced by the aforesaid bacteria in said sample, by comparing the respective values of the intensity of the aforesaid anodic current obtained for the fractions cultured in parallel in culture media A, B, C, D, E and F, and optionally the culture media B' and C', with the respective values obtained for a reference bacterial strain.

The method of the present invention can be used in the development of novel antibiotics of the family of the β-lactam antibiotics in particular for investigating the stability of the molecule with respect to different beta-lactamases.

The present invention is illustrated in more detail by the figures and the examples given hereunder.

BRIEF DESCRIPTION OF THE DRAWINGS

FIG. 10A: strain producing carbapenemase OXA-48. FIG. 10B: strain producing carbapenemase of type OXA-48+CTX-M. FIG. 10C: strain producing carbapenemase of type NDM-1. FIG. 10D: strain producing carbapenemase of type KPC-2.

DETAILED DESCRIPTION

Figure 1:
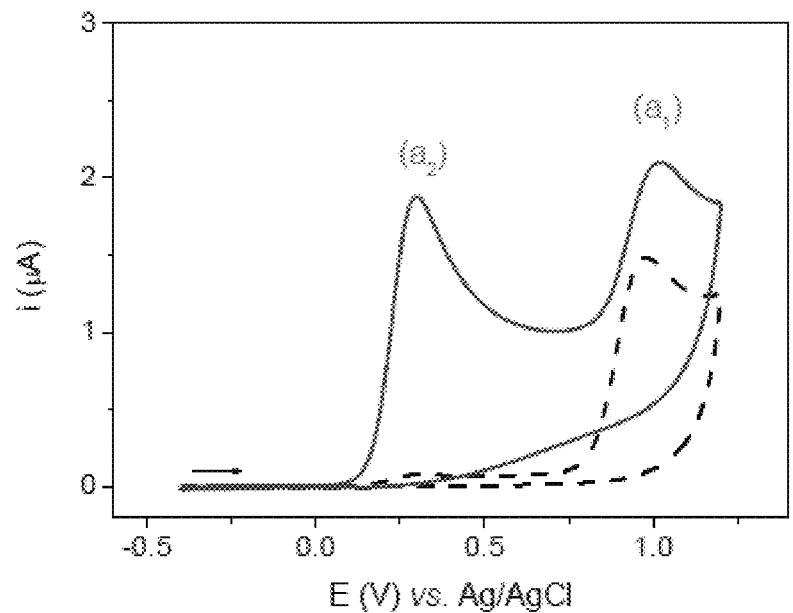
FIG. 1: Cyclic voltammograms ($v=50$ mV·s$^{-1}$) obtained for a 500-µM solution of nitrocefin in PBS in the absence (dotted line) and in the presence of ESBL (solid line) after incubation for 10 min.

Example I: Identification of Beta-Lactamase-Producing Bacteria Using Nitrocefin as Substrate 1. Materials and Methods 1.1. Reagents and Solutions The phosphate buffer (PBS; 100 mM; pH=7.0) and all the aqueous solutions are prepared with Milli-Q 18-MΩ water (Millipore purification system).

The culture medium, comprising Luria broth (LB, 10 g·L$^{-1}$ of Bacto tryptone, 5 g·L$^{-1}$ of Bacto yeast extract, 5 g·L$^{-1}$ of NaCl), is prepared in the laboratory and sterilized by autoclaving at 120° C.

The nitrocefin is purchased from Merck Millipore (Reference 484400). A stock solution of nitrocefin at $10^{-2}$ M is prepared in dimethylsulphoxide (DMSO) and then stored in the form of 50-µL aliquots at −20° C.

The sodium salt of cefotaxime (Reference C 7039-100 mg) and the clavulanate potassium (Reference 33454-100 mg) are supplied by Sigma-Aldrich. Stock solutions at 1 mg·mL$^{-1}$ are prepared daily in PBS.

The ESBL was extracted from a strain of *E. coli* isolated in the Bacteriology Laboratory of the Dijon University Hospital Centre (1485; type CTX-M-1).

The *E. coli* strain K12 and ESBL-producing *E. coli* strain (MIAE6690) are from the collection of strains of the Dijon centre of the French National Institute for Agricultural Research (INRA). Samples of these strains are stored at −80° C. in the form of 500-µL aliquots containing 50% of bacterial suspension and 50% of glycerol (v/v).

1.2. Measuring Instruments and Electrodes 1.2.1. For the Proof of Concept

The electrochemical measurements are carried out with a PGSTAT12 Autolab potentiostat (Metrohm) controlled by GPES software (version 4.9).

The sensors are prepared with a manual screen printing machine (Circuit Imprimé Français, Bagneux, France) with carbon ink (Electrodag® PF 407A, Acheson Colloids). A series of 6 sensors is printed on flexible polyester film by causing the ink to pass through a screen frame (120 wires/cm) using a scraper. After a drying step (1 hour at 65° C.), the sensors are stored at ambient temperature.

Each sensor consists of the working electrode and a counter-electrode. The working area of the sensor (7.07 mm$^2$) is delimited with an adhesive ring, which also allows the electrochemical cell to be defined. For carrying out amperometric measurement, the sensor is inserted in a connector (Dropsens) connected to the potentiostat, and then a 20-µL drop of the solution to be analyzed is deposited on the surface of the sensor. After immersing a silver wire coated with a silver chloride precipitate (Ag/AgCl), which constitutes the reference electrode, the measurements are carried out by cyclic voltammetry (v=50 mV·s$^{-1}$) at ambient temperature.

1.2.2 For Distinguishing the Beta-Lactamases in Blood Samples and Quantification of the ESBL-Producing Strains:

The voltammetric measurements (v=50 mV·s$^{-1}$) are carried out by depositing 30-µL drops of solution on screen-printed carbon sensors supplied by Dropsens (DRP-110) connected beforehand to a PSTAT mini 910 portable potentiostat (Methrohm) with power supply from the computer's USB port and controlled by the PSTAT software (version 1.0).

1.3. Amperometric Detection of Beta-Lactamase Activity

5 µL of ESBL solution is put in a polypropylene tube containing 45 µL of 0.5 mM nitrocefin solution in phosphate buffer (PBS; 100 mM; pH=7.0). After a step of incubation for 10 minutes at ambient temperature in the dark, 20 µL of the mixture is taken and transferred onto the surface of the screen-printed carbon sensor. A reference electrode (Ag/AgCl) is then immersed in the 20 µL of solution previously deposited, and the cyclic voltammetry measurements are carried out by proceeding as follows: potential scanning between −0.4 V and 1.2 V at a rate of 50 mV·s$^{-1}$.

The oxidation peak appearing at about +0.3 V results from hydrolysis of the beta-lactam ring of nitrocefin and may be selected as the analytical response for identifying beta-lactamases in a sample.

1.4. Amperometric and Colorimetric Measurement of ESBL Activity with Nitrocefin

45 µL of nitrocefin solution (0.5 mM in PBS) is put in a polypropylene tube containing 5 µL of the ESBL solution previously diluted in PBS. The reaction mixture is incubated for 10 min at ambient temperature in the dark. The product of the enzymatic reaction is then detected by amperometry and spectrophotometry. The electrochemical measurement is carried out by transferring 20 µL of the mixture onto the surface of the screen-printed carbon sensor in order to carry out the voltammetric measurement as stated above. The intensity of the oxidation peak current measured at about +0.3 V vs. Ag/AgCl is selected as the analytical response. For spectrophotometric detection, the solution is diluted in PBS (by a factor of 5) and then pipetted into single-use cuvettes (Ratiolab® Q-VETTES semimicro, No. 2712120) before carrying out measurement of absorbance at λ=520 nm with a DU® 800 spectrophotometer (Beckman Coulter).

1.5. Detection of a Beta-Lactamase-Producing Strain

10 µL of the *E. coli* strain K12 (ESBL$^-$) that does not produce beta-lactamases and 10 µL of the *E. coli* strain MIAE6690 that is ESBL-producing (ESBL$^+$) are cultured in parallel in a tube containing 10 mL of LB medium supplemented with cefotaxime (4 µg·mL$^{-1}$) for 4.5 h at 37° C. Then 1 mL of each bacterial suspension is transferred to a polypropylene tube and centrifuged at 7000 g for 10 min. After removing the supernatant, a volume of 50 µL of nitrocefin solution (0.5 mM in PBS) is put in the tube and incubated with the bacterial pellet for 10 min at ambient temperature in the dark. The liquid is then aspirated and transferred onto the screen-printed sensor to carry out the voltammetric measurement as stated in section 1.3.

1.6. Identification of Strains Resistant to the Third-Generation Cephalosporins in Blood Cultures The blood cultures supplied by the Bacteriology Laboratory of Dijon University Regional Hospital Centre are blood samples that have been cultured either in Bactec™ bottles suitable for testing for mainly aerobic microorganisms, or in Bactec™ bottles intended specifically for growing mainly anaerobic bacteria.

Volumes of 10 µL of sample are introduced in parallel into tubes containing 10 mL of LB medium (Medium A), 10 mL of LB medium supplemented with cefotaxime at 4 µg·mL$^{-1}$ (Medium B) and 10 mL of LB medium supplemented with cefotaxime at 4 µg·mL$^{-1}$ and clavulanic acid at 100 µg·mL$^{-1}$ (Medium C). After an incubation step at 37° C. with stirring for 2 hours, 5 mL of the contents of each tube is taken with a syringe and then filtered using a manual filtration device (Swinnex®, 13 mm, Millipore) equipped with a membrane with a pore size of 0.45 µm (HVLP, 13 mm, Millipore). Each filter is then placed at the bottom of a well of a polystyrene microplate (24-well plate, Cellstar®, 662160), into which 80

μL of nitrocefin solution (0.5 mM in PBS) is then introduced, and left to incubate for 10 min at ambient temperature in the dark.

40 μL of each mixture is taken and transferred onto the surface of a screen-printed carbon sensor (Dropsens, DRP-110) connected beforehand to a PSTAT mini 910 portable potentiostat (Methrohm) with power supply from the computer's USB port and controlled by the PSTAT software (version 1.0). Linear voltammetry measurements are carried out by linear potential scanning from −0.1 V to 1.2 V at a rate of 50 mV·s$^{-1}$.

The peak current (I) appearing at about +0.3 V, associated with hydrolysis of the beta-lactam ring of nitrocefin, is selected as the analytical response. By comparing the values of current i measured for each sample incubation condition (Medium A, B, C), it is possible to draw a conclusion about whether or not the strain is able to produce a cefotaxime-hydrolyzing enzyme.

1.7. Quantification of the Extended-Spectrum Beta-Lactamase (ESBL)-Producing Strains in Wastewater 1.7.1. Construction of a Calibration Curve for ESBL-Producing *E. coli* in Water from Purification Works 10 μL of the ESBL-producing *E. coli* strain MIAE6690 is cultured in a tube containing 10 mL of LB culture medium supplemented with cefotaxime (4 μg·mL$^{-1}$) overnight at 42° C., with stirring. The concentration of bacteria in the culture thus obtained ($S_0$) is determined by making serial dilutions in a TS medium containing tryptone (10 g·L$^{-1}$) and NaCl (5 g·L$^{-1}$) and then spreading the solutions on dishes containing an agar medium (35.6 g·L$^{-1}$ Tryptone Bile X-glucose, 4 mg·L$^{-1}$ cefotaxime).

The culture $S_0$ is diluted in series (dilution factors comprised between 10 and $10^8$) in a sample of water from a purification works (either raw, or treated) autoclaved beforehand, preparing solution volumes of 1 mL in polypropylene tubes.

Then 500 μL of these previously diluted solutions (dilution factors comprised between $10^4$ and $10^8$) are introduced separately into a tube containing 25 mL of LB medium supplemented with cefotaxime at 4 μg·mL$^{-1}$ and incubated at 42° C. with stirring for 4 hours. A volume of 500 μL of the previously autoclaved sample of water from the purification works (either raw, or treated), used for making the dilutions of the bacterial strain, is incubated under the same conditions (negative control). Volumes of 10 mL are then taken in duplicate from each tube with a syringe and then filtered separately using a manual filtration device (Swinnex®, 13 mm, Millipore) equipped with a membrane with a pore size of 0.45 μm (HVLP, 13 mm, Millipore). Each filter is then placed at the bottom of a well of a polystyrene microplate (24-well plate, Cellstar®, Reference: 662160), into which 80 μL of nitrocefin solution (0.5 mM in PBS) is then introduced, and left to incubate for 15 min at ambient temperature in the dark.

40 μL of the contents of each well is taken and transferred onto the surface of a screen-printed carbon sensor (Dropsens, DRP-110) connected beforehand to a PSTAT mini 910 portable potentiostat (Methrohm), and the linear voltammetry measurements are carried out as mentioned in section 1.6.

1.7.2. Detection of the ESBL-Producing Strains in Samples of Water From Purification Works Volumes of wastewater (1-10 mL) and of treated water (20-100 mL) are filtered in duplicate on membranes with a pore size of 0.45 μm (HAWP, 47 mm, Millipore) using a stainless-steel filtration ramp (Sartorius Combisart). For each sample, one of the membranes is put in a tube containing 25 mL of LB medium supplemented with cefotaxime at 4 μg·mL$^{-1}$ (Medium B) whereas the second is immersed in a tube containing 25 mL of LB medium supplemented with cefotaxime at 4 μg·mL$^{-1}$ and clavulanic acid at 10 μg·mL$^{-1}$ (Medium C). All the tubes are incubated at 42° C. with stirring for 4 hours and then their contents are filtered and analyzed in the presence of nitrocefin as indicated in 1.7.1.

For a given sample, the intensities of the peak currents measured at about 0.3 V for the incubations in media B and C are designated $i_B$ and $i_C$ respectively. The quantity of ESBL-producing strains is calculated from the value of current $i=i_B-i_C$ and using a calibration curve (1.7.1).

2. Results 2.1. Electrochemical Characterization of Hydrolyzed Nitrocefin

Nitrocefin was hydrolyzed by an extended-spectrum beta-lactamase in an abundant quantity. The voltammetric behaviour of nitrocefin (S) and of its hydrolyzed form (P) was investigated by cyclic voltammetry using screen-printed electrodes based on carbon. Nitrocefin and hydrolyzed nitrocefin both have a peak of irreversible anodic oxidation (a1) at about +1.0 V vs. Ag/AgCl. This peak may be attributed to oxidation of the thiol group in the dihydrothiazine group or to other functions specific to the cephalosporin derivatives. In contrast to nitrocefin, hydrolyzed nitrocefin (P) generates a peak of irreversible anodic oxidation (a2) that is well defined and is observed at a lower anode potential of about +0.3 V (FIG. 1). The presence of the a2 peak indicates the presence of hydrolyzed nitrocefin and may therefore be selected as the analytical response for demonstrating the activity of the extended-spectrum beta-lactamase.

2.2. Measurement of the Activity of the ESBLs

Figure 2:
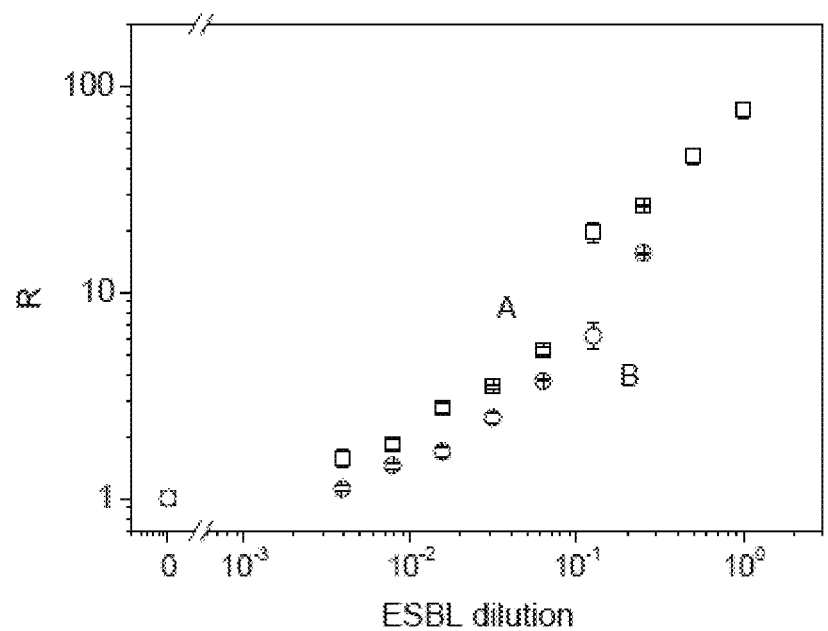
FIG. 2: Calibration curve (log-log) of an ESBL, the quantities of which are determined by the method of cyclic voltammetry according to the invention (A, and by the spectrophotometric method (B, O). The analytical responses are recorded after incubating the ESBLs for 10 min with a 500-µM solution of nitrocefin prepared in PBS. The reaction mixtures are diluted 5-fold in PBS before carrying out the spectrophotometric measurements. The value R corresponds to the responses of current or to the optical densities, respectively, normalized with the values obtained in the absence of ESBL ($i_0=50\pm5$ nA; $OD_0=0.097\pm0.008$). The standard deviation represents the standard error of the two measurements.

The activity of the ESBLs was measured in parallel by spectrophotometric measurement and by voltammetric measurement using nitrocefin. Each series of experiments is carried out by varying the concentration of ESBLs, and the calibration curves (log-log) obtained with the electrochemical method of the invention and the spectrophotometric method are illustrated in FIG. 2. Each measurement is normalized relative to the signal obtained in the absence of ESBL. The calibration curve obtained by the voltammetric method shows that this method allows quantitative detection of the activity of ESBLs with sensitivity close to that of the spectrophotometric method. Moreover, the voltammetric method of the invention offers a wider region of linearity. The reproducibility of the spectrophotometric measurement and that of the voltammetric measurement are similar.

Figure 3:
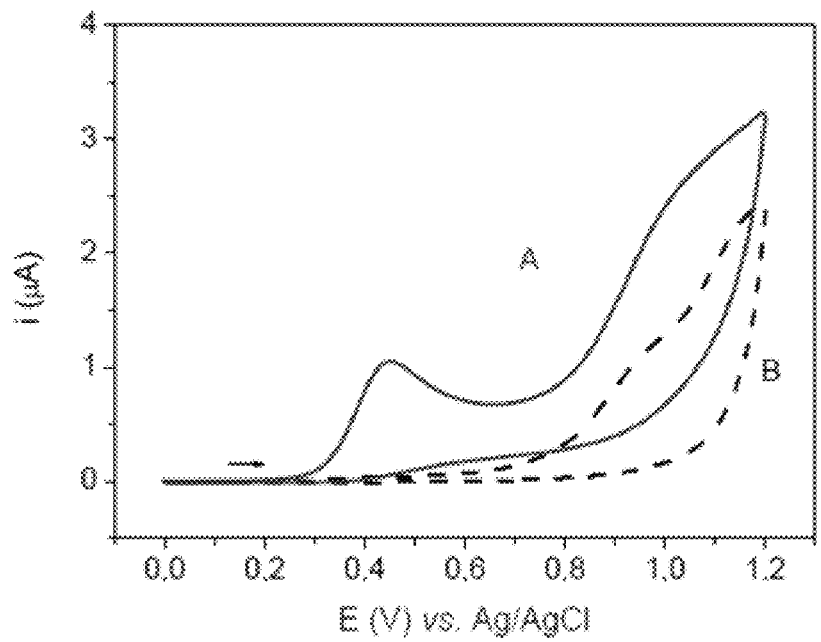
FIG. 3: Voltammetric curves ($v=50$ mV·s$^{-1}$) recorded on a screen-printed sensor for the *E. coli* strains ESBL$^+$ (A) and ESBL$^-$ (B), cultured at 37° C. for 4.5 h in a culture medium containing 4 µg·mL$^{-1}$ of cefotaxime after centrifugation (1 mL; 7000 g; 10 min) and incubation of the pellet for 10 min with 50 µL of a 500-µM solution of nitrocefin in PBS.

2.3. Detection of the ESBL-Producing Strains of *E. coli* by Measurement by Cyclic Voltammetry To evaluate the capacity of the voltammetric method for detecting the ESBL-producing bacteria, two strains of *E. coli* with a well-characterized genotype were selected, one being a producer of an ESBL (ESBL$^+$) and the other not producing ESBL (ESBL$^-$). First the two strains are cultured in LB medium containing 4 μg·mL$^{-1}$ of cefotaxime. After the centrifugation step, the respective bacterial pellets of these two strains are incubated with nitrocefin as substrate. FIG. 3 shows the voltammetric responses obtained for the ESBL$^+$ strain (curve A) and the ESBL$^-$ strain (curve B), respectively. Curve A has an anodic peak at about +0.4 V vs. Ag/AgCl, associated with catalytic hydrolysis of the β-lactam ring of nitrocefin by the ESBL$^+$ strain, whereas no peak is recorded for the ESBL$^-$ strain. This result is in good agreement with the values of optical density of 0.934 and 0.002 obtained for the ESBL$^+$ strain and the ESBL$^-$ strain, respectively. The culture medium supplemented with cefotaxime and the medium without antibiotic were also subjected to voltammetric measurement. No specific signal is observed in the potential range [0.1-0.6 V vs. Ag/AgCl] for these two media, which confirms that neither the LB culture medium, nor cefotaxime interferes with voltammetric detection.

2.4. Distinguishing ESBL-Producing Bacteria

Figure 4:
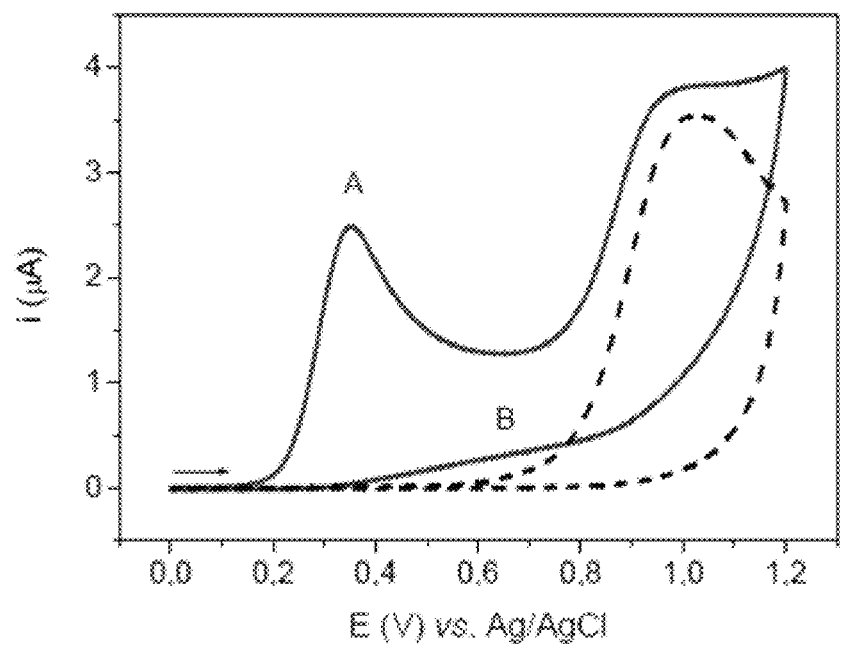
FIG. 4: Cyclic voltammograms ($v=50$ mV·s$^{-1}$) recorded with a screen-printed sensor for the *E. coli* strain ESBL$^+$ cultured in a culture medium containing only 4 µg·mL$^{-1}$ of cefotaxime (A) or supplemented with 10 µg·mL$^{-1}$ of clavulanate potassium, then centrifuged (1 mL; 7000 g; 10 min) before a step of incubation of the pellet with 50 µL in a 500-µM solution of nitrocefin in PBS for 10 min.

Since the hyperproduced cephalosporinases and the carbapenemases can also hydrolyse cefotaxime, the bacteria producing these enzymes can also give a positive response in the presence of cefotaxime. In order to distinguish the bacteria producing extended-spectrum beta-lactamases and the bacteria producing hyperproduced cephalosporinases and carbapenemases, the bacteria were cultured simultaneously in two culture media, one containing cefotaxime as antibiotic, the other additionally containing clavulanate potassium as inhibitor of ESBLs. After recovering the bacteria, the bacterial pellets were incubated with nitrocefin as substrate. The voltammetric curves recorded by cyclic voltammetry are presented in FIG. 4. The anodic peak resulting from hydrolysis of nitrocefin was observed for an ESBL$^+$ strain cultured with cefotaxime (curve A), whereas no signal was recorded for the same strain cultured in the presence of clavulanate potassium (curve B). This result confirms the presence of ESBL-producing bacteria.

This result is in agreement with the values obtained for the E. coli count on selective medium, since the latter are 80 CFU·mL$^{-1}$ for a culture supplemented with an inhibitor and $1.8 \times 10^8$ CFU·mL$^{-1}$ for a culture without inhibitor, respectively.

2.5. Quantification of the Beta-Lactamase-Producing Bacteria

Figure 5:
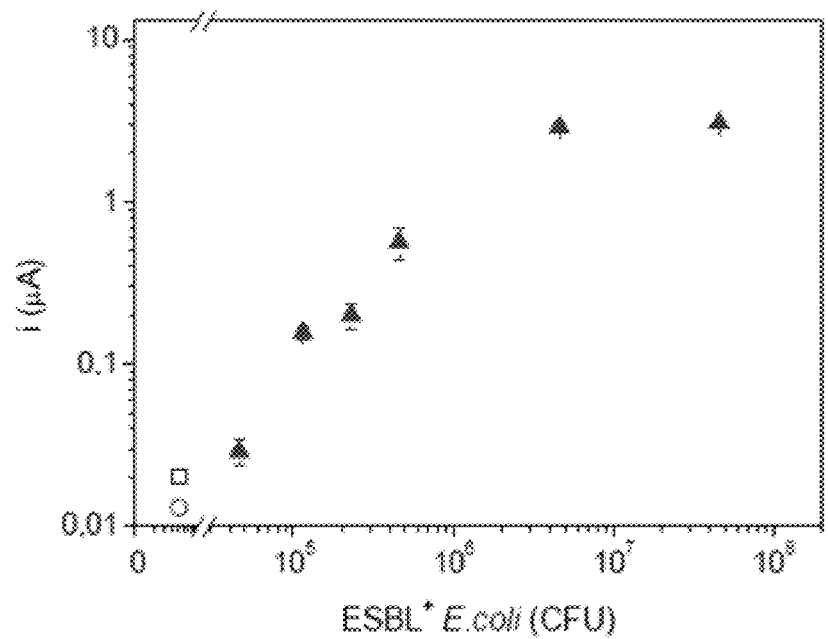
FIG. 5: Calibration curve of the ESBL$^+$ strain after incubation at 37° C. for 3.5 h in an LB culture medium supplemented with 4 µg·mL$^{-1}$ of cefotaxime. After serial dilution of the bacterial culture, volumes of 10 mL are filtered in duplicate. The bacteria recovered after filtration are incubated for 10 min with 80 µL of the 500-µM solution of nitrocefin in PBS. The x-axis corresponds to the number of bacteria recovered after filtration. The error bars represent the standard deviation of two experiments. The open square (□) represents the negative control consisting of the ESBL$^+$ strain cultured with 4 µg·mL$^{-1}$ of cefotaxime and 10 µg·mL$^{-1}$ of clavulanic acid. The open circle (○) corresponds to the signal from non-hydrolyzed nitrocefin.
Figure 6:
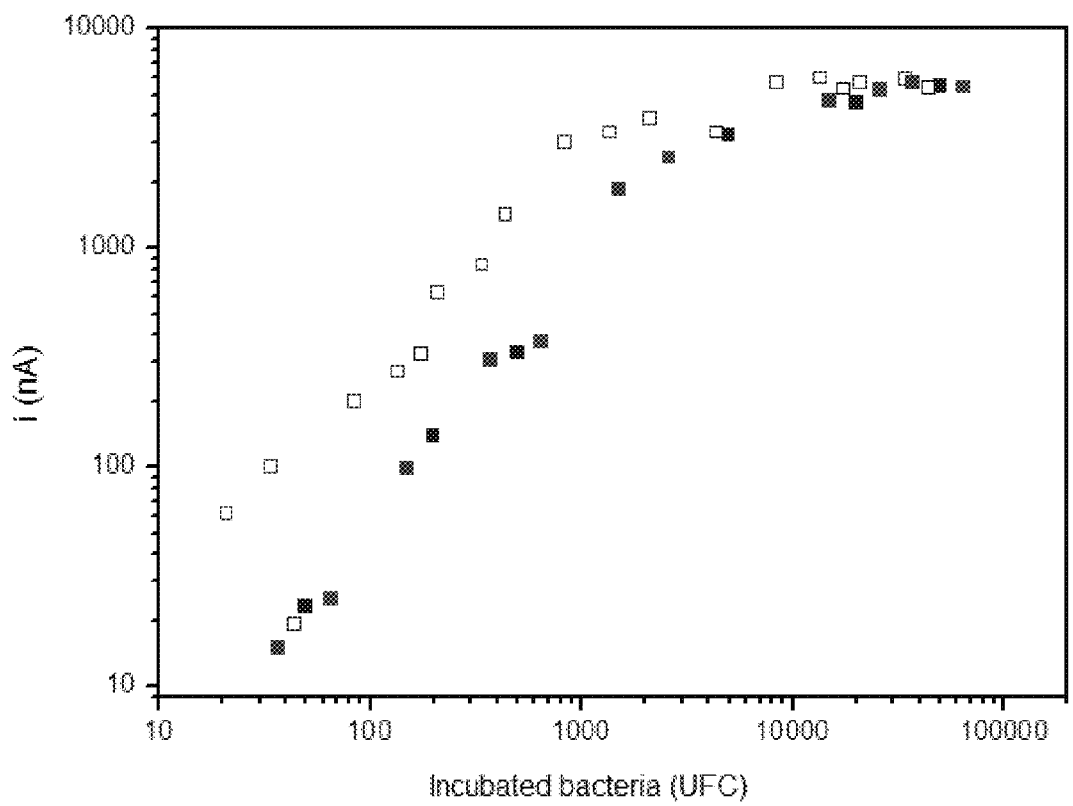
FIG. 6: Calibration curves of an *E. coli* strain producing ESBLs carried out in three samples of raw wastewater (■) and three samples of previously autoclaved treated water (|). The value i (nA) corresponds to the current of the oxidation peak of hydrolyzed nitrocefin recorded for a bacterial count from which that measured for the negative control had been subtracted.

The capacity of the method of the invention for quantitative determination of ESBL-producing bacteria was evaluated by serial dilution of a culture of ESBL$^+$ E. coli from $5 \times 10^4$ to $5 \times 10^7$ CFU·mL$^{-1}$, incubated with cefotaxime. The calibration curve in FIG. 5 has a wide region of linearity, allowing quantitative determination of the ESBL-producing bacterial strains to be envisaged. The plateau observed at high concentrations of ESBL-producing bacteria suggests that all of the nitrocefin initially present is hydrolyzed.

2.6. Quantification of the Beta-Lactamase-Producing Bacteria in Raw or Autoclaved Wastewater The calibration curves for ESBL-producing E. coli are established for the samples of raw wastewater and the samples of previously autoclaved treated water by the method described in section 1.7.1. These calibration curves are used for quantifying the ESBL-producing bacteria in raw water and in water treated by the method of the invention, respectively. As shown in Tables 1 and 2, the results obtained with a method of the invention are in agreement with the results obtained by counting bacteria.

TABLE 1

Determination of the ESBL-producing strains (CFU · L$^{-1}$) in raw water from 5 purification works in Côte d'Or (A, B, C, D, E).

| | Counting | Method described in the invention |
|---|---|---|
| A | $2 \times 10^5$ | $1.2 \times 10^5$ |
| B | $7 \times 10^5$ | $6 \times 10^5$ |
| C | $1 \times 10^5$ | $2.2 \times 10^5$ |
| D | $8 \times 10^5$ | $5 \times 10^5$ |
| E | $3.5 \times 10^5$ | $4 \times 10^5$ |

TABLE 2

Determination of the ESBL-producing strains (CFU · L$^{-1}$) in treated water from 5 purification works in Côte d'Or (A, B, C, D, E).

| | Counting | Method described in the invention |
|---|---|---|
| A | $2.5 \times 10^3$ | $1 \times 10^3$ |
| B | $1 \times 10^4$ | $2 \times 10^4$ |
| C | $4 \times 10^3$ | $4 \times 10^3$ |
| D | $1.8 \times 10^3$ | $5 \times 10^3$ |
| E | $5 \times 10^4$ | $4 \times 10^4$ |

2.7. Distinguishing the Beta-Lactamases

Five bacterial strains obtained from clinical samples and producing different types of beta-lactamases (penicillinases, ESBL of type CTX-M, inducible cephalosporinase, hyperproduced cephalosporinase) were analyzed by the method of the invention.

Each bacterial strain, as well as the negative control, were incubated in three different culture media respectively (media A, B and C): medium A is an LB culture medium, medium B is an LB culture medium containing 4 µg·mL$^{-1}$ of cefotaxime, and medium C is an LB culture medium containing 4 µg·mL$^{-1}$ of cefotaxime and 100 µg·mL$^{-1}$ of clavulanic acid. After filtration of the bacterial suspensions with Swinnex®, the filtration membranes on which the bacteria were recovered were incubated in the dark for 10 min with 80 µL of nitrocefin at 500 µM.

Measurement by cyclic voltammetry was implemented using carbon electrodes. The peaks of anodic current corresponding to the oxidation of hydrolyzed nitrocefin for these three media are designated $i_A$, $i_B$ and $i_C$, respectively.

The results obtained with the strains producing the various beta-lactamases are presented in FIGS. 7A to 7F.

Figure 7A:
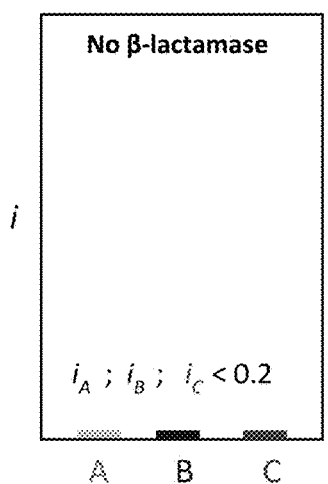
FIGS. 7A, 7B, 7C, 7D, 7E, 7F: Profiles of the oxidation currents (pA) of hydrolyzed nitrocefin recorded for different types of beta-lactamases and used for distinguishing the beta-lactamases in medical samples (blood cultures, isolated strains).

The results in FIG. 7A correspond to the response of a sample that contains a strain that does not produce beta-lactamases (negative).

Figure 7B:
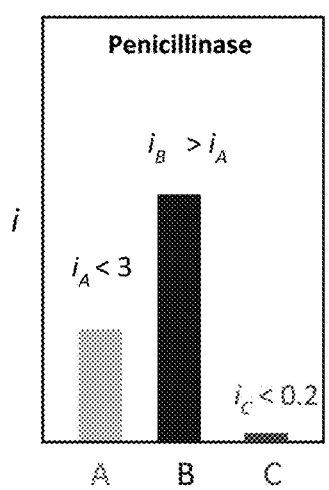
Figure 7C:
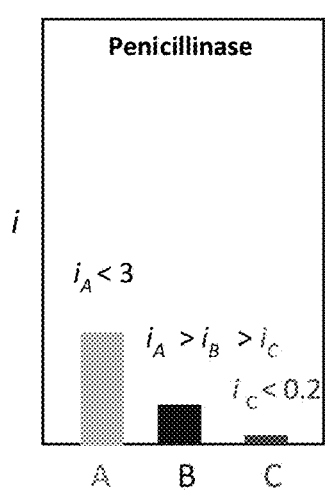
Figure 7D:
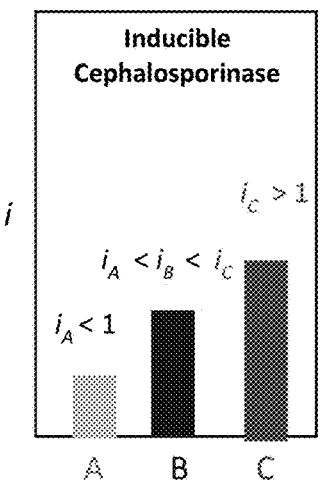
Figure 7E:
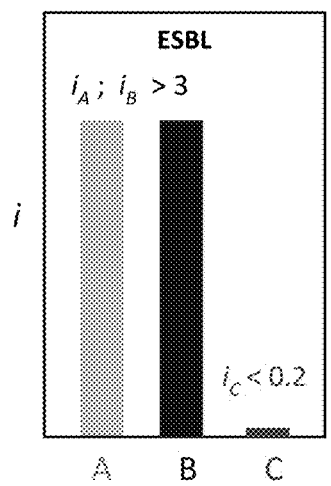
Figure 7F:
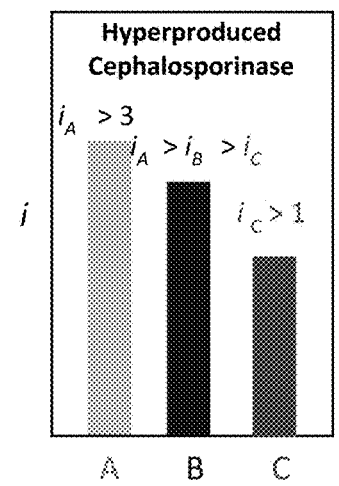

The results in FIGS. 7B and 7C correspond to two penicillinases. The catalytic activity of a penicillinase is characterized by the presence of the anodic current of hydrolyzed nitrocefin obtained for the bacteria originating from media A and B and the absence of the specific anodic current for the bacteria from medium C.

An inducible cephalosporinase (FIG. 7D) is characterized by the peaks of anodic current of hydrolyzed nitrocefin obtained in these three media corresponding to the following criteria: $i_A < 1$, $i_A < i_B < i_C$, and $i_C > 1$.

An extended-spectrum beta-lactamase of the CTX-M type (FIG. 7E) is characterized by the peaks of anodic current of hydrolyzed nitrocefin obtained in these three media corresponding to the following criteria: $i_A > 3$, $i_B > 3$, and $i_C < 0.2$.

A hyperproduced cephalosporinase (FIG. 7F) is characterized by the peaks of anodic current of hydrolyzed nitrocefin obtained in these three media corresponding to the following criteria: $i_A > 3$, $i_A > i_B > i_C$, and $i_C > 1$.

An agar diffusion antibiogram and the amperometric method of the invention are used respectively for distinguishing the beta-lactamase-producing bacteria in blood culture samples. As can be seen from the results presented in Table 3 below, the degree of overlap of the method of the present invention with the antibiogram is 100%.

TABLE 3

Comparison of the results obtained after obtaining an antibiogram (ATB) and implementing the electrochemical method of the invention for distinguishing the beta-lactamase-producing strains in blood culture broths.

| Sample No. | Flora | ATB | Electrochemistry* |
|---|---|---|---|
| 035 | Escherichia coli | C3G and others: S | $i_A$ = 0.15 - $i_B$ = 0.13 - $i_C$ = 0.15 No beta-lactamase C3G and others: S |
| 034 | Escherichia coli | C3G: R (ESBL) | $i_A$ = 5.1 - $i_B$ = 3.1 - $i_C$ = 0.17 ESBL C3G: R |
| 033 | Escherichia coli | C3G: R (ESBL) | $i_A$ = 3.7 - $i_B$ = 3.1 - $i_C$ = 0.18 ESBL C3G: R |
| 030 | Proteus mirabilis | C3G: S (Penicillinase) | $i_A$ = 2 - $i_B$ = 0.3 - $i_C$ = 0.18 Penicillinase C3G: S |
| 029 | Escherichia coli | C3G: S (Penicillinase) | $i_A$ = 1.3 - $i_B$ = 2.2- $i_C$ = 0.16 Penicillinase C3G: S |
| 026 | Escherichia coli | C3G and others: S (no beta-lactamase) | $i_A$ = 0.16 - $i_B$ = 0.14 - $i_C$ = 0.14 No beta-lactamase C3G and others: S |
| 025 | Escherichia coli | C3G: S (Penicillinase) | $i_A$ = 1.4 - $i_B$ = 1.5 - $i_C$ = 0.2 Penicillinase C3G: S |
| 024 | Escherichia coli | C3G: S (Penicillinase) | $i_A$ = 0.7 - $i_B$ = 1.5 - $i_C$ = 0.15 Penicillinase C3G: S |
| 019 | Escherichia coli | C3G and others: S | $i_A$ = 0.17 - $i_B$ = 0.17 - $i_C$ = 0.16 No beta-lactamase C3G and others: S |
| 005 | Escherichia coli | C3G: S (Penicillinase) | $i_A$ = 0.42 - $i_B$ = 0.96 - $i_C$ = 0.18 Penicillinase C3G: S |

*$i_A$, $i_B$, and $i_C$ (µA)

An agar diffusion antibiogram and the amperometric method of the invention are also implemented for distinguishing beta-lactamase-producing bacteria, obtained from various biological samples, after isolation thereof on Drigalski lactose agar. The results presented in Table 4 show that the degree of overlap of the method of the present invention with the antibiogram is 100%.

TABLE 4

Comparison of the results obtained after carrying out an antibiogram (ATB) and implementing the electrochemical method of the invention for distinguishing the beta-lactamase-producing strains previously isolated on Drigalski medium.

| Sample No. | Flora | ATB | Electrochemistry* |
|---|---|---|---|
| 018 | Enterobacter cloacae | C3G: S Inducible cephalosporinase | $i_A$ = 0.23 - $i_B$ = 0.27 - $i_C$ = 1.3 Inducible cephalosporinase C3G: S |
| 014 | Escherichia coli | C3G: R (ESBL) | $i_A$ = 5.5 - $i_B$ = 5.6 - $i_C$: 0.23 ESBL C3G: R |
| 013 | Escherichia coli | C3G: R (ESBL) | $i_A$ = 5.8 - $i_B$ = 5.6 - $i_C$ = 0.13 ESBL C3G: R |
| 012 | Escherichia coli | C3G: R (ESBL) | $i_A$ = 5.0- $i_B$ = 3.1 - $i_C$ = 0.19 ESBL C3G: R |
| 008 | Klebsiella oxytoca (urine) | C3G: S (Penicillinase) | $i_A$ = 0.25 - $i_B$ = 0.55 - $i_C$ = 0.24 Penicillinase C3G: S |
| 007 | Proteus mirabilis (bone) | C3G: S (Penicillinase) | $i_A$ = 0.14 - $i_B$ = 1.3- $i_C$ = 0.16 Penicillinase C3G: S |
| 004 | Proteus mirabilis (pus) | C3G: S (Penicillinase) | $i_A$ = 2.8 - $i_B$ = 3.4 - $i_C$ = 0.4 Penicillinase C3G: S |

*$i_A$, $i_B$, and $i_C$ (µA)

Example II: Identification of C3G-Resistant Bacteria Using the Compound HMRZ-86 as Substrate 1. Materials and Methods:
1.1. Reagents and Solutions The compound HMRZ-86 was synthesized and supplied by Kanto Chemical (Japan). A stock solution at $10^{-2}$ M is prepared in DMSO and stored in the form of 50-µL aliquots at −20° C.

The strains used in this example, presented in Table 5 below, are from the collection of cryopreserved strains of the Dijon centre of the French National Institute for Agricultural Research (INRA).

TABLE 5

| | Resistance to the beta-lactam antibiotics | |
|---|---|---|
| Species | Phenotype | Genotype |
| Escherichia coli | Wild-type | No gene |
| Escherichia coli | Penicillinase | |
| Citrobacter freundii | Inducible cephalosporinase | |
| Escherichia coli | ESBL | CTX-M15 |
| Klebsiella pneumoniae | ESBL | CTX-M15 |
| Serratia marcescens | Hyperproduced cephalosporinase | |
| Klebsiella pneumoniae | Carbapenemase | OXA 48 -CTXM |

1.2. Identification of the C3G-Resistant Strains in Liquid Cultures

Each cryopreserved strain is cultured in 10 mL of LB medium at 37° C. until the stationary phase is obtained.

A volume of 50 µL of culture liquid is incubated in the presence of 50 µL of a solution of HMRZ-86 at 0.5 mM in PBS at 37° C. with stirring for 30 min. 40 µL of the reaction mixture is taken and transferred onto the surface of a screen-printed carbon sensor (Dropsens, DRP-110) connected beforehand to a STAT 8000P portable potentiostat (Dropsens) with power supply from the computer's USB port and controlled by the DropView 8400 software. Linear voltammetry measurements are carried out by linear potential scanning from −0.1 V to 1.2 V at a rate of 50 mV·s⁻¹. The peak current appearing in the potential range +0.2 to +0.55 V vs. Ag/AgCl, associated with hydrolysis of the beta-lactam ring of HMRZ-86, is selected as the analytical response. If the intensity of the peak (i) has a value above 500 nA, the sample contains a strain capable of degrading the C3Gs.

1.3. Producing a Calibration Curve of ESBL-Producing Strains of *E. coli* in Autoclaved Wastewater Samples The protocol described in 1.7.1. of Example I was implemented with a single culture condition (LB supplemented with cefotaxime at 4 μg·mL⁻¹). The filters are incubated with 90 μL of HMRZ-86 (0.25 mM in PBS) at 37° C. for 30 min. The measurements are carried out by linear voltammetry as mentioned above (section 1.2). The peak current appearing in the potential range +0.2 to +0.55 V vs. Ag/AgCl, associated with hydrolysis of the beta-lactam ring of HMRZ-86, is selected as the analytical response. Its intensity (I) is proportional to the quantity of C3G-resistant strains present in the sample.

2. Results 2.1. Electrochemical Characterization of HMRZ-86 and its Hydrolyzed Forms A solution of HMRZ-86 was incubated with different bacterial strains resistant or sensitive to the C3Gs, i.e. able or unable to hydrolyse the HMRZ-86 molecule, respectively.

Figure 8:
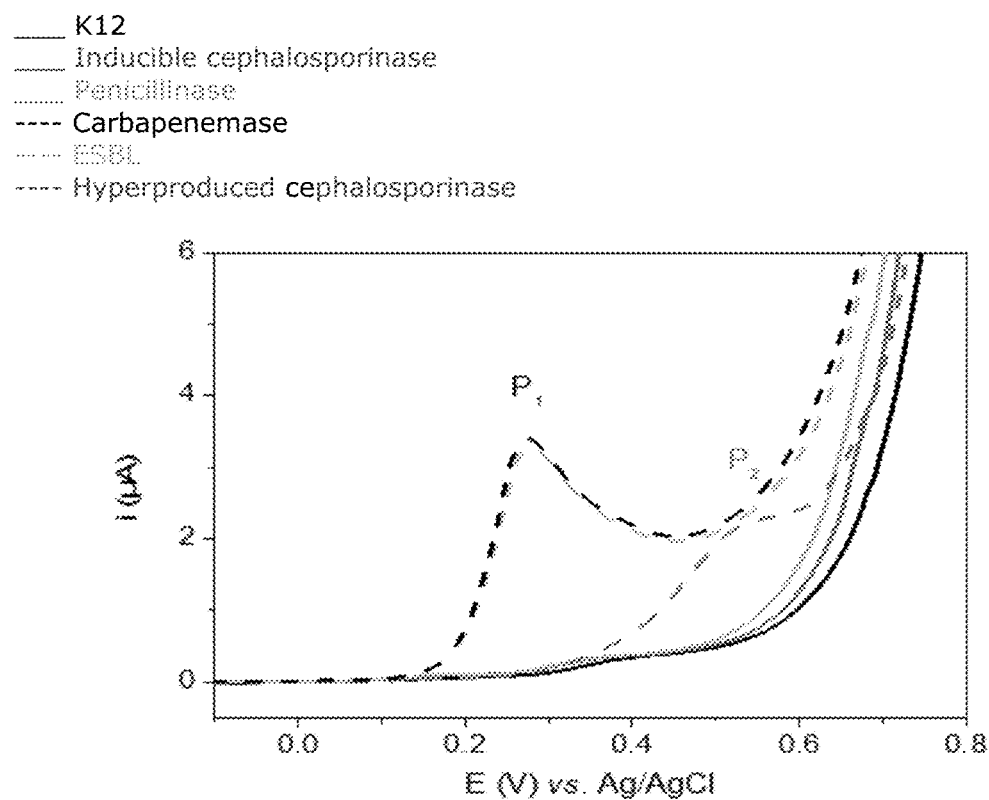
FIG. 8: Cyclic voltammograms ($v=50$ mV·s$^{-1}$) recorded for six liquid cultures ($v=50$ µL) containing, respectively, a strain that does not produce beta-lactamase (K12), a strain producing inducible cephalosporinase, a strain producing penicillinase, a strain producing ESBL, a strain producing hyperproduced cephalosporinase, a strain producing carbapenemase after incubation with 50 µL of HMRZ-86 (0.5 mM in PBS) for 30 min.

The voltammetric responses of HMRZ-86 and of its hydrolyzed forms are presented in FIG. 8. The voltammograms recorded for HMRZ-86 incubated with the C3G-sensitive strains (not producing beta-lactamase, producing penicillinase or inducible cephalosporinase) all have the same profile with two waves of oxidation of very low intensity around +0.2 and +0.4 V vs. Ag/AgCl, which disappear in favour of well-defined oxidation peaks for the hydrolyzed forms of HMRZ-86. More precisely, hydrolysis of HMRZ-86 by the strains producing ESBL and carbapenemases leads to a product that has a quite specific oxidation peak P1 (FIG. 8) at about +0.25 V vs. Ag/AgCl, whereas the product resulting from hydrolysis of HMRZ-86 by a strain producing hyperproduced cephalosporinase is oxidized specifically at ~+0.5 V vs. Ag/AgCl to give a peak P2 (FIG. 8). Thus, the presence of the peaks P1 or P2 indicates the presence of hydrolyzed HMRZ-86 and may be selected as the analytical response for detecting the C3G-resistant strains. Moreover, the peak P2 allows specific identification of the strains producing hyperproduced cephalosporinases.

Figure 9:
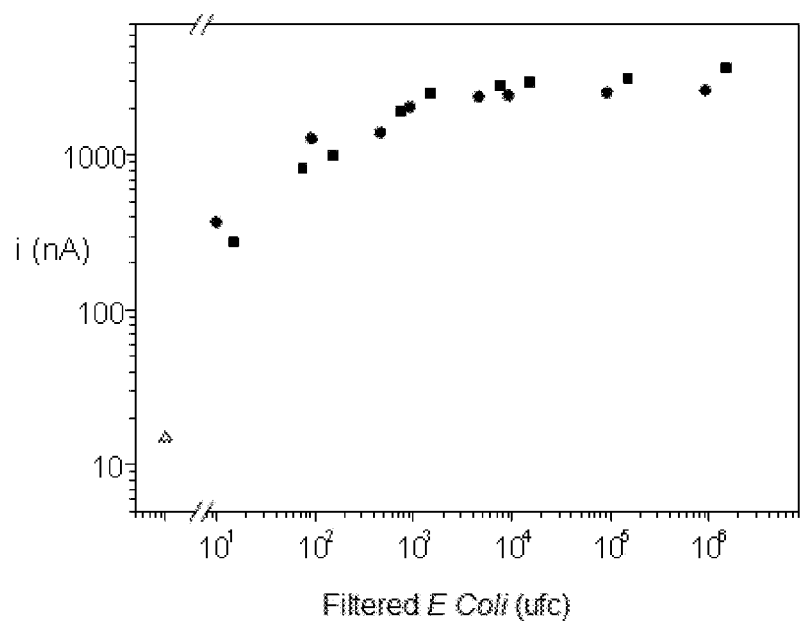
FIG. 9: Curves of calibrations carried out with two *E. coli* strains producing ESBL (type CTX-M15) represented respectively by the symbols ■ and ● in a sample of autoclaved wastewater. The value i (nA) corresponds to the peak current of oxidation of HMRZ-86, from which that measured for the negative control with a mean value of 235±15 nA (Δ) had been subtracted.
Figure 10A:
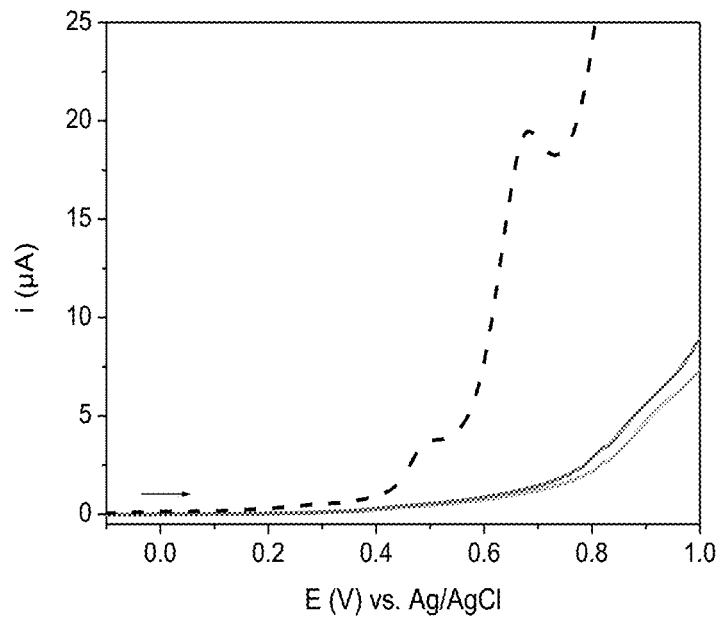
FIGS. 10A, 10B, 10C, 10D: Each figure shows the cyclic voltammograms ($v=50$ mV·s$^{-1}$) recorded for three solutions of Carba-S (30 µL) incubated at 37° C. for 30 min respectively with a strain producing ESBL, a strain producing hyperproduced cephalosporinases and a strain producing carbapenemases.
Figure 10B:
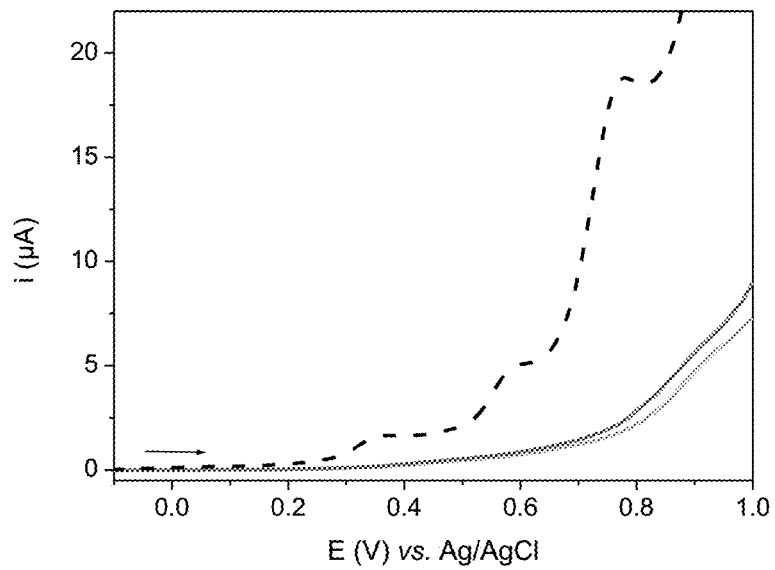
Figure 10C:
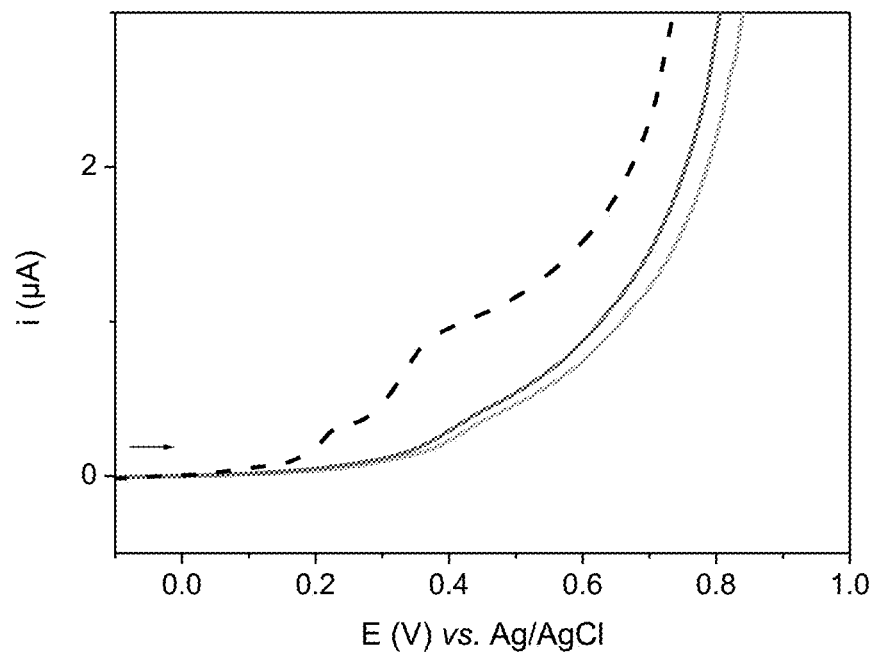
Figure 10D:
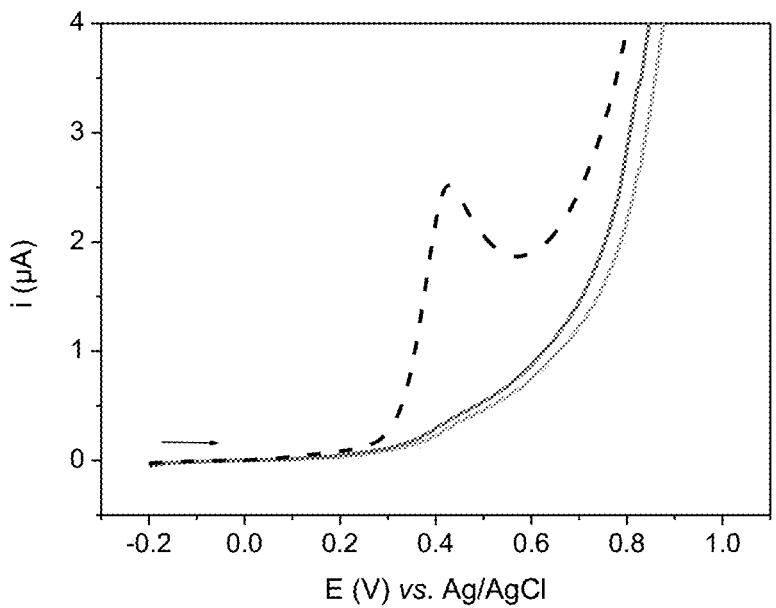
Figure 11:
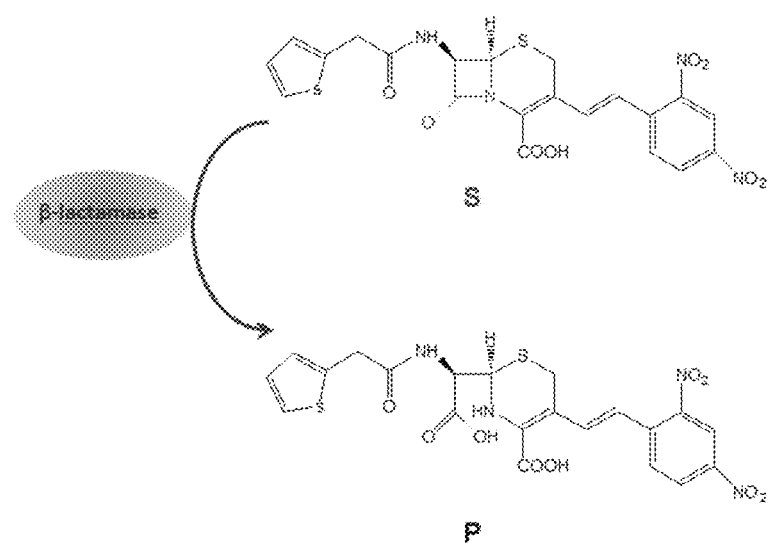
FIG. 11: this figure illustrates hydrolysis of the beta-lactam ring of nitrocefin by a beta-lactamase.

2.2. Quantification of the C3G-Resistant Strains: Example of Calibration Curves of ESBL-Producing Strains in Autoclaved Wastewater The capacity of the method of the invention for quantitative determination of the C3G-resistant bacteria with the substrate HMRZ-86 was evaluated by applying the calibration curve established according to protocol 1.3. described in the present example. FIG. 9 presents the calibration curves obtained for two ESBL-producing strains of *E. coli* (type CTX-M15) inoculated in samples of previously autoclaved wastewater. With a region of linearity comprised between 10 and 1000 bacteria filtered, this method makes it possible to envisage quantification of C3G-resistant strains with good sensitivity.

Example III: Identification of Carbapenem-Resistant Bacteria

1. Materials and Methods:

1.1. Reagents

The substrate designated "Carba-S" hereunder and its diluent correspond respectively to reagents R2 and R3 of the β CARBA™ Test kit marketed by Biorad. The Carba-S solution is prepared by adding 550 μL of R3 to R2.

The strains used in this example, presented in Table 6 below, are from the collection of cryopreserved strains of the Dijon centre of the French National Institute for Agricultural Research (INRA).

TABLE 6

| Species | Resistance to the beta-lactam antibiotics | |
|---------|-----------|----------|
|         | Phenotype | Genotype |
| *Klebsiella pneumoniae* | ESBL | CTX-M15 |
| *Serratia marcescens* | Hyperproduced cephalosporinase | |
| *Klebsiella pneumoniae* | Carbapenemase | OXA 48 -CTXM |
| *Escherichia coli* | Carbapenemase | OXA-48 |
| *Klebsiella pneumoniae* | Carbapenemase | KPC-2 |
| *Klebsiella pneumoniae* | Carbapenemase | NDM-1 |

1.2. Identification of Carbapenem-Resistant Strains Starting from Isolated Colonies Each cryopreserved strain is cultured on Muller Hinton agar at 37° C.

A 1-μL loop is incubated in the presence of 30 μL of the Carba-S solution at 37° C. with stirring for 30 min. 40 μL of the reaction mixture is taken and transferred onto the surface of a screen-printed carbon sensor (Dropsens, DRP-110) connected beforehand to a STAT 8000P portable potentiostat (Dropsens) with power supply from the computer's USB port and controlled by the DropView 8400 software. Linear voltammetry measurements are carried out by linear potential scanning from −0.1 V to 1.2 V at a rate of 50 mV·s⁻¹. The peak current (i) appearing at about +0.3-0.8 V vs. Ag/AgCl, associated with hydrolysis of the Carba-S, is selected as the analytical response. The presence of the peak (i) with an intensity above 200 nA makes it possible to conclude that a carbapenemase-producing strain is present.

2.2. Results:

2.1. Electrochemical Characterization of the Substrate Carba-S and of its Hydrolyzed Forms Starting from Isolated Colonies The solution of Carba-S was incubated with different bacterial strains sensitive or resistant to the carbapenems, i.e. able or unable to degrade the Carba-S molecule, respectively, and analyzed by linear voltammetry with screen-printed sensors.

The voltammetric responses recorded for colonies sensitive to carbapenems (producers of ESBL and of hyperproduced cephalosporinases) and carbapenemase-producing colonies of the type OXA 48, OXA 48+CTXM, KPC-2 and NDM-1 are presented, respectively (FIGS. 10A, 10B, 10C and 10D). Comparison of the voltammograms shows that only the curves recorded for the carbapenemase-producing strains have one to three waves of oxidation with well-defined peaks in a potential range from +0.2 to +0.8 V vs. Ag/AgCl. Thus, using voltammetric measurement, it is possible to distinguish Carba-S from its degradation products and therefore detect the presence of carbapenemase-producing strains.

Example IV: Comparative Results

Comparative Assay 1

The electrochemical method of the invention was applied to analysis of a panel of 40 strains producing various β-lactamases and was compared with the R-Lacta™ Test (Biorad), the principle of which is based on qualitative colorimetric detection of the C3G-resistant strains. The results presented in Table 7 were obtained after 30 min of incubation of the bacteria with the substrate HMRZ-86 for both methods. Based on the interpretation of the results proposed by the supplier, the R-Lacta™ Test allows identification of the C3G-resistant strains with a level of agreement of 68%, whereas a level of agreement of 95% was obtained with the electrochemical method of the invention. In contrast to colorimetry, amperometry offers the advantage of measuring a numerical value of current which, on the one hand, avoids any subjective interpretation of the result (intermediate colour), and on the other hand allows traceability of the result.

Table 7: Comparison of the results obtained with the electrochemical method of the invention for liquid cultures with those obtained with the R-Lacta™ Test implemented according to the supplier's recommendations with isolated colonies. In both cases, the readings were taken after incubation with the substrate HMRZ-86 for 30 min.

TABLE 7

| Resistance to the beta-lactam antibiotics | | | β-Lacta™ Test[a] | Quantity of bacteria analyzed | Electrochemical assay[b] Intensity |
|---|---|---|---|---|---|
| Phenotype | Genotype | Species | Colour | (CFU) | (nA) |
| Beta-lactamase negative | | *E. coli* K12 | Yellow | $7.3 \times 10^7$ | 302 |
| Beta-lactamase negative | | *P. mirabilis* 11747 | Yellow | — | 322 |
| Low-level penicillinase | | *P. mirabilis* 11768 | Yellow | — | 233 |
| Low-level penicillinase | | *K. pneumoniae* 11770 | Yellow | $7.15 \times 10^7$ | 365 |
| Low-level penicillinase | | *K. oxytoca* 11779 | Yellow | $5.35 \times 10^7$ | 412 |
| Low-level penicillinase | | *E. coli* 11781 | Yellow | $3.8 \times 10^7$ | 377 |
| Hyperproduced penicillinase | | *E. coli* 11746 | Yellow | $3.75 \times 10^7$ | 380 |
| Hyperproduced penicillinase | | *E. coli* 11765 | Yellow | $3.1 \times 10^7$ | 323 |
| Hyperproduced penicillinase | | *E. coli* 11771 | Yellow | $7.05 \times 10^7$ | 362 |
| Hyperproduced penicillinase | | *E. coli* 11780 | Yellow | $5.15 \times 10^7$ | 425 |
| Inducible cephalosporinase | | *C. freundii* 11745 | Yellow | $2.95 \times 10^7$ | 369 |
| Inducible cephalosporinase | | *E. coli* 11748 | Yellow | $4.65 \times 10^7$ | 424 |
| Inducible cephalosporinase | | *E. coli* 11766 | Yellow | $7.65 \times 10^7$ | 408 |
| Inducible cephalosporinase | | *E. aerogenes* 11772 | Yellow | $9.5 \times 10^7$ | 362 |
| Inducible cephalosporinase | | *E. coli* 11776 | Yellow | $3.7 \times 10^7$ | 446 |
| Hyperproduced cephalosporinase | | *P. aeruginosa* 11774 | Orange | $5.3 \times 10^7$ | 2160 |
| Hyperproduced cephalosporinase | | *E. aerogenes* 11775 | Yellow | $9.45 \times 10^7$ | 501 |
| Hyperproduced cephalosporinase | | *P. aeruginosa* 11778 | Yellow | $7.4 \times 10^7$ | 2278 |
| Hyperproduced cephalosporinase | | *P. aeruginosa* 11782 | Yellow | $5.95 \times 10^7$ | 1778 |
| Hyperproduced cephalosporinase | | *E. cloacae* 11784 | Orange | $7.95 \times 10^7$ | 569 |
| Hyperproduced cephalosporinase | | *S. marcescens* 11787 | Orange | $8.55 \times 10^7$ | 3922 |
| Hyperproduced cephalosporinase | | *E. cloacae* 11790 | Orange | $5.15 \times 10^7$ | 686 |
| Hyperproduced cephalosporinase | | *E. coli* 11791 | Yellow | $5.15 \times 10^7$ | 816 |
| Hyperproduced cephalosporinase | | *E. cloacae* 11794 | Orange | $7.95 \times 10^7$ | 842 |
| ESBL | TEM 24 | *E. aerogenes* 11796 | Orange | $5.7 \times 10^7$ | 1249 |
| ESBL | CTX-M-1 | *E. coli* 11810 | Red | $8.05 \times 10^7$ | 2544 |
| ESBL | CTX-M-15 | *K. pneumoniae* 11812 | Red | $5.35 \times 10^7$ | 3494 |
| ESBL | CTX-M-2 | *E. coli* 11817 | Red | $5.25 \times 10^7$ | 1472 |
| ESBL | CTX-M-1 | *E. coli* 11818 | Red | $4.25 \times 10^7$ | 3583 |
| ESBL | SHV-12 | *E. coli* 11820 | Red | $5.95 \times 10^7$ | 1249 |
| ESBL | CTX-M-27 | *E. coli* 11828 | Red | $4.15 \times 10^7$ | 2640 |

TABLE 7-continued

| Resistance to the beta-lactam antibiotics | | | β-Lacta™ Test[a] | Quantity of bacteria analyzed | Electrochemical assay[b] Intensity |
|---|---|---|---|---|---|
| Phenotype | Genotype | Species | Colour | (CFU) | (nA) |
| ESBL | CTX-M-9 | E. coli 11833 | Red | $4.7 \times 10^7$ | 2455 |
| ESBL | TEM-12 | E. coli 11834 | Yellow | $2.85 \times 10^7$ | 418 |
| ESBL | CTX-M-14 | E. coli 11863 | Red | $2.95 \times 10^7$ | 2544 |
| Carbapenemase | OXA-48 - CTX-M | K. pneumoniae 11754 | Red | $6.4 \times 10^7$ | 3520 |
| Carbapenemase | OXA-48 - CTX-M | E. coli 11755 | Red | $6.75 \times 10^7$ | 3509 |
| Carbapenemase | OXA-48 | E. coli 11757 | Orange | $9.45 \times 10^7$ | 625 |
| Carbapenemase | OXA-48 | K. pneumoniae 11762 | Orange | $4.95 \times 10^7$ | 476 |
| Carbapenemase | KPC-2 | K. pneumoniae 11839 | Red | $3.2 \times 10^7$ | 1567 |
| Carbapenemase | NDM-1 | K. pneumoniae 11842 | Red | $3.55 \times 10^7$ | 1257 |

[a] Yellow or orange colour: negative result (absence of C3G-resistant strains). Red colour: positive result (presence of C3G-resistant strains)
[b] i < 490 nA: negative result (absence of C3G-resistant strains), i > 490 nA: positive result (presence of C3G-resistant strains). The value of i = 490 nA corresponds to the mean value of the 12 responses obtained for the strains producing penicillinases and inducible cephalosporinases, to which 3 times the standard deviation was added.

Comparative Assay 2

The electrochemical method of the invention was applied to the analysis of a panel of 28 strains producing ESBL, hyperproduced cephalosporinase and carbapenemases and was compared with the β-Carba™ Test (Biorad), the principle of which is based on qualitative colorimetric detection of the carbapenem-resistant strains. The results presented in Table 8 were obtained after 30 min of incubation of a 1-μL loop of colonies isolated with the Carba-S substrate for both methods. Relying on the interpretation of the results proposed by the supplier, the β-Carba™ Test allows identification of the carbapenem-resistant strains with a level of agreement of 43%, whereas with the electrochemical method of the invention a level of agreement of 100% was obtained. Once again, because of numerical measurement of current, the electrochemical method of the invention avoids any subjective interpretation of the result (intermediate colour), and makes it possible to obtain a reliable result much more quickly than by colorimetry.

TABLE 8

Table 8: Comparison of the results obtained for analysis of isolated colonies with the electrochemical method of the invention and with the β-Carba™ Test applied according to the supplier's recommendations. In both cases, the readings were taken after incubation with the substrate Carba-S for 30 min.

| Resistance to the beta-lactam antibiotics | | | β-Carba™ Test[a] | Electrochemical assay[b] Intensity |
|---|---|---|---|---|
| Phenotype | Genotype | Species | Colour | (nA) |
| ESBL | CTX-M-15 | E. coli 11808 | Yellow | 77 |
| ESBL | CTX-M-14 | E. coli 11806 | Yellow | 148 |
| ESBL | CTX-M-1 | E. coli 11810 | Yellow | 132 |
| ESBL | CTX-M-15 | K. pneumoniae 11812 | Yellow | 128 |
| ESBL | CTX-M-2 | E. coli 11817 | Yellow | 147 |
| ESBL | CTX-M-1 | E. coli 11818 | Yellow | 118 |
| ESBL | CTX-M-14 | E. coli 11823 | Yellow | 137 |
| ESBL | CTX-M-14 | E. coli 11824 | Yellow | 128 |
| ESBL | CTX-M-14 | E. coli 11826 | Yellow | 130 |
| Hyperproduced cephalosporinase | | E. coli 11791 | Yellow | 93 |
| Carbapenemase | OXA-48 - CTX-M | K. pneumoniae 11749 | Orange | 4103 |
| Carbapenemase | OXA-48 - CTX-M | K. pneumoniae 11752 | Yellow | 2281 |
| Carbapenemase | OXA-48 - CTX-M | E. coli 11753 | Yellow | 1055 |
| Carbapenemase | OXA-48 - CTX-M | K. pneumoniae 11754 | Yellow | 1129 |
| Carbapenemase | OXA-48 - CTX-M | E. coli 11755 | Orange | 1836 |
| Carbapenemase | OXA-48 - CTX-M | K. pneumoniae 11756 | Orange | 2616 |
| Carbapenemase | OXA-48 - CTX-M | E. coli 11764 | Yellow | 1281 |
| Carbapenemase | OXA-48 | E. coli 11750 | Yellow | 741 |
| Carbapenemase | OXA-48 | E. coli 11757 | Yellow | 716 |
| Carbapenemase | OXA-48 | E. coli 11758 | Orange | 1458 |
| Carbapenemase | OXA-48 | K. pneumoniae 11761 | Yellow | 1191 |
| Carbapenemase | OXA-48 | K. pneumoniae 11762 | Yellow | 791 |
| Carbapenemase | OXA-48 | E. coli 11763 | Yellow | 1033 |
| Carbapenemase | KPC-2 | K. pneumoniae 11839 | Red | 3437 |
| Carbapenemase | KPC-2 | K. pneumoniae 11840 | Orange | 3427 |
| Carbapenemase | KPC-2 | K. pneumoniae 11841 | Red | 3731 |

TABLE 8-continued

Table 8: Comparison of the results obtained for analysis of isolated colonies with the electrochemical method of the invention and with the β-Carba ™ Test applied according to the supplier's recommendations. In both cases, the readings were taken after incubation with the substrate Carba-S for 30 min.

| Resistance to the beta-lactam antibiotics | | | β-Carba ™ Test[a] | Electrochemical assay[b] Intensity |
|---|---|---|---|---|
| Phenotype | Genotype | Species | Colour | (nA) |
| Carbapenemase | NDM-1 | K. pneumoniae 11842 | Orange | 1761 |

[a]Yellow or orange colour: negative result (absence of production of carbapenemases). Colour bright orange or red or purple: positive result (presence of production of carbapenemases)
[b]i < 195 nA: negative result (absence of production of carbapenemases). i > 195 nA: positive result (presence). The value i = 195 nA corresponds to the mean value of the 10 responses obtained for the strains that do not produce carbapenemases, to which 3 times the standard deviation was added.

The invention claimed is:

1. A method for in-vitro determination of the presence of bacteria producing beta-lactamases, in a sample, said method comprising the following steps:
   (a) incubating said sample in a medium containing a substrate of the beta-lactamases, said substrate having electrochemical properties, said substrate being nitrocefin or the compound HMRZ-86 (E isomer of (6R, 7R)-trifluoroacetate 7-[[2-(2-amino-4-thiazolyl)-2-[(1-carboxy-1-methylethoxy)imino]acetyl]amino]-1-aza-3-[2-(2,4-dinitrophenyl)ethenyl]-8-oxo-5-thiabicyclo [4.2.0]oct-2-ene-2-carboxylic acid),
   (b) applying an amperometric measurement, comprising a cyclic voltammetric method, by using a working electrode based on carbon or based on a noble metal or based on metal oxide, to the aforesaid medium obtained at the end of step (a) and to a negative control, respectively,
   (c) measuring the difference of value of the intensity of the anodic current corresponding to oxidation of the hydrolyzed substrate, and that of the negative control.

2. The method according to claim 1, characterized in that said method comprises the following steps:
   (a) incubating the sample in a medium containing a substrate of the beta-lactamases, the substrate having amperometric properties;
   (b) applying an amperometric measurement to the aforesaid medium obtained at the end of step (a) and to a negative control, respectively; and
   (c) determining the presence of the beta-lactamase-producing bacteria by measuring the difference between the value of the intensity of the anodic current corresponding to oxidation of the hydrolyzed substrate, measured for the aforesaid medium obtained at the end of step (a), and the value of the intensity of the anodic current measured for the negative control.

3. The method according to claim 2, said method additionally comprising, after step (c), step (d) consisting of measuring the difference between the value of the intensity of the anodic current measured for said medium obtained at the end of step (a) and a calibration curve established under the same conditions.

4. The method according to claim 1 making it possible in addition to distinguish the type of beta-lactamases selected from penicillinases, extended-spectrum beta-lactamases, inducible cephalosporinases, hyperproduced cephalosporinases and carbapenemases, produced by the aforesaid bacteria in a sample that may contain them, said method comprising the following steps:
   (a) incubating, in parallel, a fraction of the aforesaid sample in:
      a culture medium A, a culture medium B and a culture medium C:
         culture medium A being a basic culture medium,
         culture medium B being a basic culture medium supplemented with a third-generation cephalosporin, and
         culture medium C being a basic culture medium supplemented with a cephalosporin and a penicillinase inhibitor, and
      optionally in a culture medium B', a culture medium C', a culture medium D, a culture medium E:
         culture medium B' being a basic culture medium supplemented with a third-generation cephalosporin different from that present in medium B;
         culture medium C' being culture medium B' supplemented with a penicillinase inhibitor;
         culture medium D being a basic culture medium supplemented with a cephalosporin and a cephalosporinase inhibitor, and
         culture medium E being a basic culture medium supplemented with a carbapenem,
   (b) incubating, in parallel, the aforesaid culture media obtained at the end of the incubation in step (a) in a medium containing nitrocefin; and
   (c) applying an amperometric means, to the aforesaid media obtained at the end of step (b) and thereby determining the presence of beta-lactamase-producing bacteria and distinguishing the type of beta-lactamases.

5. The method according to claim 4 in order to determine the presence of the bacteria producing an extended-spectrum beta-lactamase, said method comprising the following steps:
   (a) incubating, in parallel, a fraction of the aforesaid sample in a culture medium A, a culture medium B and a culture medium C, and optionally in a culture medium B' and a culture medium C', as defined according to claim 4;
   (b) incubating, in parallel, the aforesaid culture media obtained at the end of the incubation in step (a) in a medium containing nitrocefin; and
   (c) applying an amperometric means, to the aforesaid media obtained at the end of step (b) in order to determine the presence of the bacteria producing an extended-spectrum beta-lactamase.

6. The method according to claim 4, in order to determine and distinguish the beta-lactamase-producing bacteria in a sample that may contain them, comprising the following steps:
   (a) incubating, in parallel, a fraction of the aforesaid sample in a culture medium A, a culture medium B, a culture medium C, a culture medium D, a culture medium E, optionally a medium B' and a medium C', as defined according to claim 4;
   (b) incubating, in parallel, the aforesaid culture media obtained at the end of the incubation in step (a) in a medium containing nitrocefin;
   (c) applying an amperometric measurement to the aforesaid media obtained at the end of step (b) and to a negative control, respectively;
   (d) determining the presence of beta-lactamase-producing bacteria in said sample by comparing the value of the intensity of the anodic current corresponding to the oxidation of hydrolyzed nitrocefin obtained for the fraction cultured in culture medium A with the value of the intensity of the current obtained for the negative control; and (e) distinguishing the type of beta-lactamases produced by the aforesaid bacteria in said sample, by measuring the respective difference between the values of the intensity of the aforesaid anodic current obtained for the fractions cultured in parallel in culture media A, B, C, D and E, optionally B' and C' and the respective values obtained for a reference bacterial strain.

7. The method according to claim 6, further comprising a step (f) after step (e) making it possible to quantify beta-lactamase-producing bacteria distinguished in step (e) by measuring the difference between the value of the intensity of the anodic current corresponding to nitrocefin hydrolyzed by said beta-lactamase and a calibration curve established under the same conditions.

8. The method according to claim 4, for distinguishing the type of beta-lactamases and optionally defining the subfamily of carbapenemases produced by the aforesaid bacteria in a sample that may contain them, said method comprising the following steps:

(a) incubating, in parallel, a fraction of the aforesaid sample in a culture medium A, a culture medium B, a culture medium C, a culture medium D, a culture medium E, and a culture medium F, and optionally a culture medium B' and a culture medium C';

the media A, B, B', C, C', D, E being as defined according to claim 4;

culture medium F being a basic culture medium supplemented with a carbapenem and an inhibitor specific to a subfamily of carbapenemases;

(b) incubating, in parallel, the aforesaid culture media obtained at the end of the incubation in step (a) in a medium containing nitrocefin;

(c) applying an amperometric measurement to the aforesaid media obtained at the end of step (b) and to a negative control, respectively;

(d) determining the presence of beta-lactamase-producing bacteria in said sample by comparing the value of the intensity of the anodic current corresponding to the oxidation of hydrolyzed nitrocefin obtained for the fraction cultured in culture medium A with the value of the intensity of the current obtained for the negative control; and (e) distinguishing the type of beta-lactamases produced by the aforesaid bacteria in said sample, by measuring the respective differences between values of the intensity of the aforesaid anodic current obtained for the fractions cultured in parallel in culture media A, B, C, D, E and F, and optionally the culture media B' and C', and the respective values obtained for a reference bacterial strain.

9. The method according to claim 1, characterized in that the intensity of the anodic current corresponding to oxidation of hydrolyzed nitrocefin in a buffer of neutral pH is measured in a potential range comprised between +0.1 V and +0.5 V vs. Ag/AgCl.

10. The method according to claim 4, characterized in that the third-generation cephalosporin is selected from the group comprising cefotaxime, ceftazidime and ceftriaxone; that the penicillinase inhibitor is clavulanic acid, tazobactam or sulbactam; that said cephalosporinase inhibitor is cloxacillin; that the carbapenem is ertapenem, imipenem or meropenem; that a carbapenemase inhibitor is selected from EDTA, mercaptoacetic acid, boronic acid, or clavulanic acid.

11. The method according to claim 1, wherein the medium used in step (a) contains a beta-lactam antibiotic only hydrolyzed by extended-spectrum beta-lactamases, hyperproduced cephalosporinases and carbapenemases, after the step (b) of the amperometric measurement, said method comprising a step of determining and quantifying in vitro the presence of bacteria resistant to a third generation cephalosporin.

12. The method according to claim 1, wherein the medium used in step (a) contains the substrate that is only hydrolyzed by carbapenemases, after the step (b) of the amperometric measurement, said method comprising a step of determining and quantifying in vitro the presence of carbapenemase producing bacteria.

13. The method according to claim 1, characterized in that said sample is selected from a biological sample, a sample of environmental origin, or a food sample.

* * * * *